(12) United States Patent
Nakamura et al.

(10) Patent No.: US 10,912,681 B2
(45) Date of Patent: Feb. 9, 2021

(54) DEVICE FOR MANUFACTURING PARTICULATE-CONTAINING ARTICLE AND METHOD FOR MANUFACTURING PARTICULATE-CONTAINING ARTICLE

(71) Applicant: ZUIKO CORPORATION, Osaka (JP)

(72) Inventors: Hideyuki Nakamura, Osaka (JP); Yukihiko Fujita, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 186 days.

(21) Appl. No.: 16/073,065

(22) PCT Filed: Jan. 25, 2017

(86) PCT No.: PCT/JP2017/002499
§ 371 (c)(1),
(2) Date: Jul. 26, 2018

(87) PCT Pub. No.: WO2017/131014
PCT Pub. Date: Aug. 3, 2017

(65) Prior Publication Data
US 2019/0029890 A1 Jan. 31, 2019

(30) Foreign Application Priority Data
Jan. 27, 2016 (JP) .................................. 2016-013155

(51) Int. Cl.
| | | |
|---|---|---|
| *A61F 13/15* | (2006.01) | |
| *D06C 11/00* | (2006.01) | |
| *B32B 5/14* | (2006.01) | |
| *A61F 13/53* | (2006.01) | |
| *D04H 1/407* | (2012.01) | |
| *A61F 13/84* | (2006.01) | |
| *B05C 19/04* | (2006.01) | |

(52) U.S. Cl.
CPC .. *A61F 13/15658* (2013.01); *A61F 13/15585* (2013.01); *A61F 13/53* (2013.01);
(Continued)

(58) Field of Classification Search
CPC ................ A61F 13/53; A61F 13/15658; A61F 13/15585; A61F 13/8405; B05C 19/04;
(Continued)

(56) References Cited

U.S. PATENT DOCUMENTS

| | | | |
|---|---|---|---|
| 4,340,556 A | 7/1982 | Ciencewicki | |
| 2004/0204697 A1* | 10/2004 | Litvay | ............... A61F 13/15658 604/367 |

(Continued)

FOREIGN PATENT DOCUMENTS

| | | |
|---|---|---|
| CN | 101974829 | 2/2011 |
| EP | 0 959 164 | 11/1999 |

(Continued)

OTHER PUBLICATIONS

Extended European Search Report dated Dec. 4, 2018 in European Application No. 17744244.9.
(Continued)

*Primary Examiner* — Vishal I Patel
(74) *Attorney, Agent, or Firm* — Wenderoth, Lind & Ponack, L.L.P.

(57) ABSTRACT

A sheet conveyance device for conveying, along a conveyance path, a sheet in which a given region from an obverse surface toward a reverse side thereof is composed of a non-woven fabric, and a powder supply device for supplying a powder to at least a partial zone of the sheet, are provided. Further, a fiber-raising device for raising fibers in at least part of the powder supply zone of the sheet is provided on the conveyance path at a position upstream of the powder supply device in a conveyance direction of the sheet.

13 Claims, 8 Drawing Sheets

(52) U.S. Cl.
CPC .......... *A61F 13/8405* (2013.01); *B05C 19/04* (2013.01); *B32B 5/14* (2013.01); *D04H 1/407* (2013.01); *D06C 11/00* (2013.01)

(58) Field of Classification Search
CPC .......... D04H 1/407; D06C 11/00; B32B 5/14; B32B 2250/03; B32B 5/022; B32B 27/12; B32B 2307/726; B32B 2555/02; B32B 29/02; B32B 5/26; B32B 2264/0214; B32B 7/12; B32B 7/02
See application file for complete search history.

(56) References Cited

U.S. PATENT DOCUMENTS

2006/0048880 A1* 3/2006 Blessing ........... A61F 13/15634
156/60
2015/0351973 A1 12/2015 Tsujimoto et al.

FOREIGN PATENT DOCUMENTS

| | | |
|---|---|---|
| JP | 11-318791 | 11/1999 |
| JP | 2002-1851 | 1/2002 |
| JP | 2006-152485 | 6/2006 |
| JP | 2006-297078 | 11/2006 |
| JP | 2013-5880 | 1/2013 |
| WO | 2014/104118 | 7/2014 |

OTHER PUBLICATIONS

International Search Report dated May 9, 2017 in International (PCT) Application No. PCT/JP2017/002499.

* cited by examiner

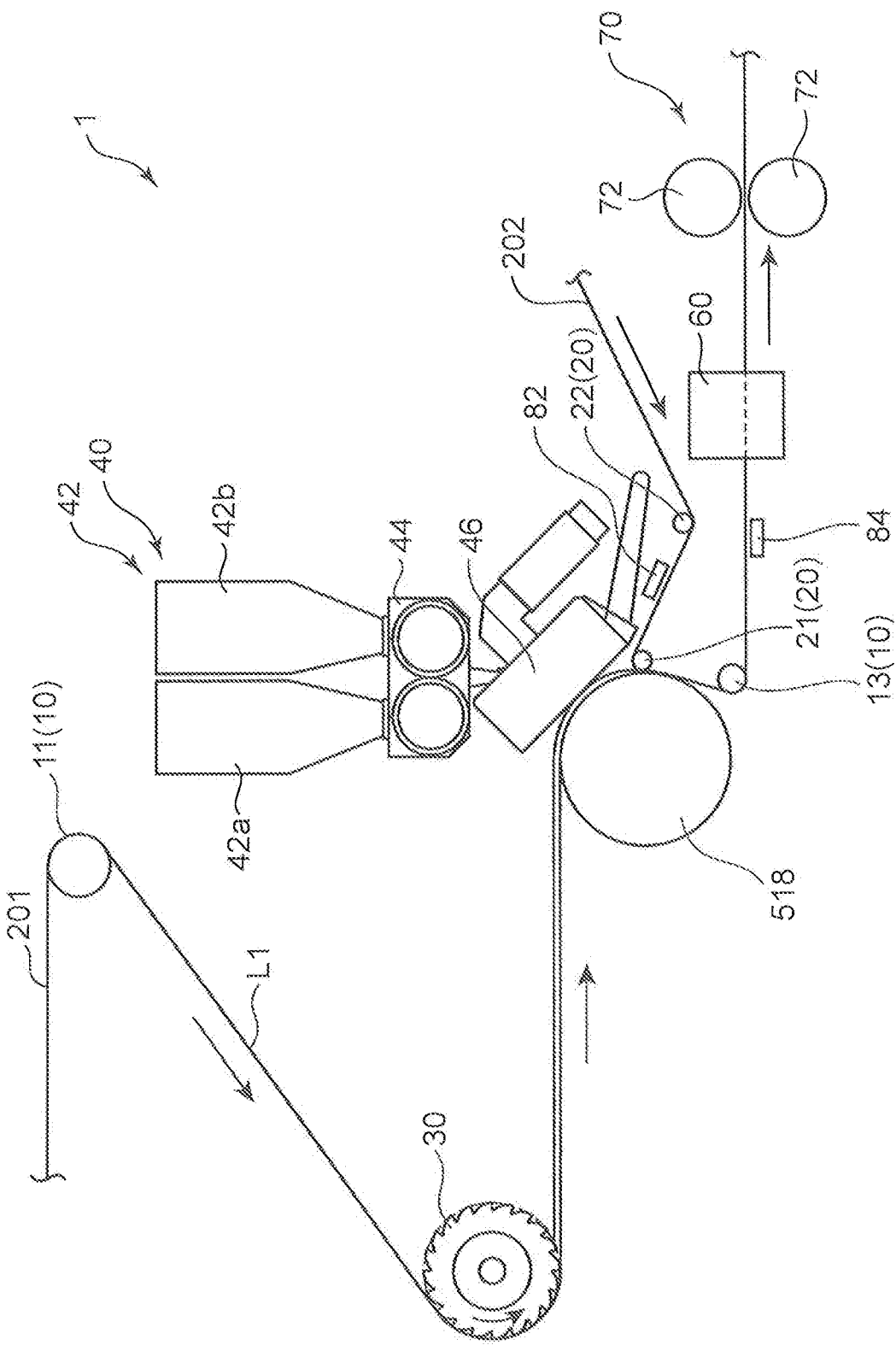

DEVICE FOR MANUFACTURING PARTICULATE-CONTAINING ARTICLE AND METHOD FOR MANUFACTURING PARTICULATE-CONTAINING ARTICLE

TECHNICAL FIELD

The present invention relates to an apparatus and method for manufacturing a powder-containing article containing a powder.

BACKGROUND ART

Heretofore, a powder-containing article containing a powder has been used in a disposable diaper or the like, in some cases. For example, a powder-containing article containing a liquid-absorbable powder has been used as an absorbent body.

As an example of an apparatus for manufacturing the powder-containing article, an apparatus described in WO 2014/104118A has been known.

The apparatus described in WO 2014/104118A comprises a shaping roll having a plurality of protruding portions on an outer peripheral surface thereof, an anvil roll having a plurality of recessed portions meshable with the protruding portions, and a device for supplying a liquid-absorbable powder to a sheet being moved on an outer peripheral surface of the anvil roll.

In the apparatus described in WO 2014/104118A, the shaping roll and the anvil roll cooperatingly form, in the sheet, a plurality of storage chambers each depressed toward a reverse side of the sheet, and particles of a powder are supplied into and stored in each of the storage chambers.

In the apparatus described in WO 2014/104118A, although the powder particles are stored in each of the receiving chambers, they are merely placed on a surface of the sheet forming a bottom surface of the storage chamber. Therefore, a powder-containing article manufactured by this apparatus has a problem that positions of the powder particles within the storage chamber are unstable. Accordingly, for example, in the case where this powder-containing article is applied to wearable article, there is a possibility that a user has an uncomfortable feeling due to displacement of the powder particles during use of the wearable article. Further, in the case where, as the above powder, a type of powder having a given function such as liquid absorbability is used, there is a possibility that the function of the powder is not adequately fulfilled because the powder particles are not stably disposed in adequate positions.

SUMMARY OF INVENTION

It is an object of the present invention to provide a manufacturing apparatus for a powder-containing article in which particles of a powder are stably disposed in adequate positions, and a manufacturing method for the powder-containing article.

Solution to Technical Problem

In order to solve the above problem, the present invention provides an apparatus for manufacturing a powder-containing article containing a powder. The apparatus comprises: a sheet conveyance device which conveys, along a conveyance path, a sheet in which a given region from an obverse surface toward a reverse side thereof is composed of a non-woven fabric; a powder supply device which is provided on the conveyance path, and supplies the powder to at least a partial zone of the sheet, from an obverse side of the sheet; and a fiber-raising device which is provided on the conveyance path at a position upstream, in a conveyance direction of the sheet, of a powder supply position where the powder is supplied to the sheet, and raises fibers in at least part of the powder supply zone of the sheet, from the obverse side of the sheet.

The present invention further provides a method for manufacturing a powder-containing article containing a powder. The method comprises: a conveyance step of conveying, along a conveyance path, a sheet in which a given region from an obverse surface toward a reverse side thereof is composed of a non-woven fabric; a powder supply step of supplying the powder to at least a partial zone of the sheet being conveyed along the conveyance path, from an obverse side of the sheet; and a fiber-raising step of raising, from the obverse side of the sheet, fibers in at least part of the powder supply zone of the sheet being conveyed along the conveyance path, at a position of the conveyance path upstream, in a conveyance direction of the sheet, of a powder supply position where the powder is supplied to the sheet.

The present invention makes it possible to manufacture a powder-containing article in which displacement of particles of the powder within the sheet is suppressed to enable the powder to be stably disposed in an appropriate position.

FIG. SB is a schematic side view depicting the first sheet just after fiber-raising.

Figure 5A:
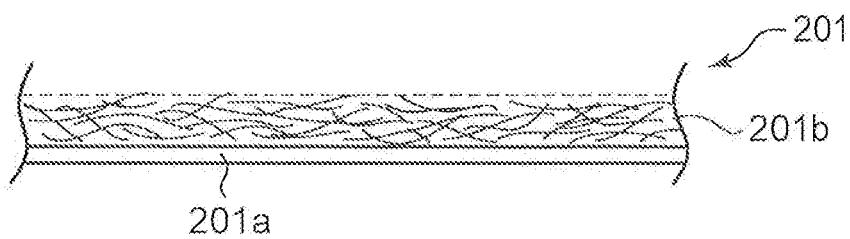
FIG. 5A is a schematic side view depicting a first sheet.
Figure 5B:
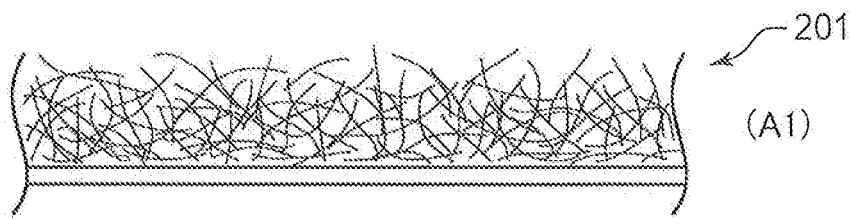
Figure 5C:
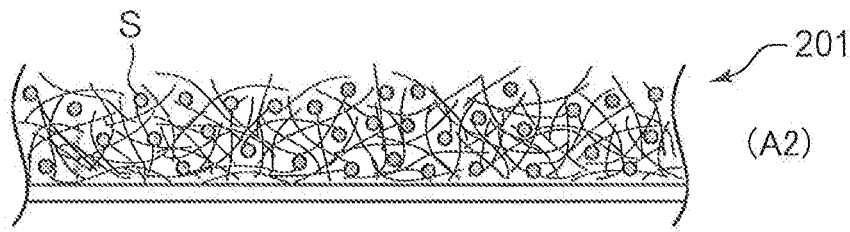

FIG. 5C is a schematic side view depicting the first sheet in a state just after a powder is supplied thereto.

Figure 5D:
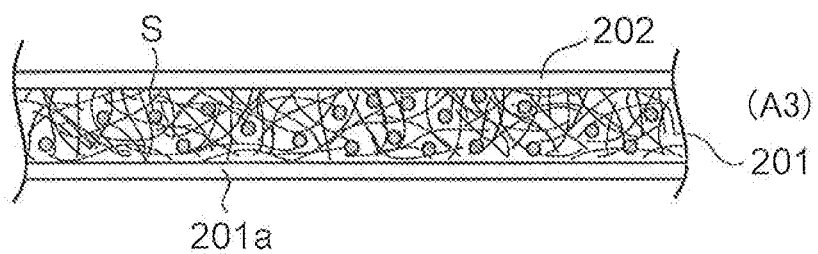

FIG. 5D is a schematic side view depicting a state just after a second sheet is set to the first sheet.

Figure 5E:
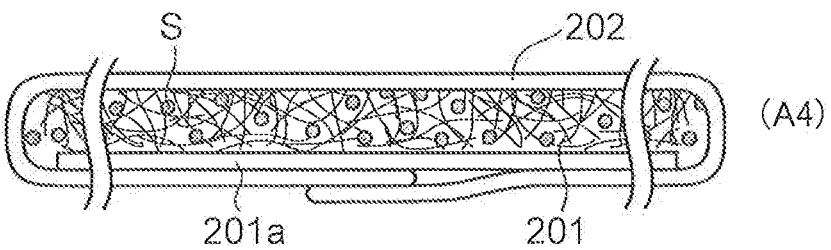

FIG. 5E is a schematic side view depicting a state just after the first sheet and the second sheet are bonded together.

Figure 5F:
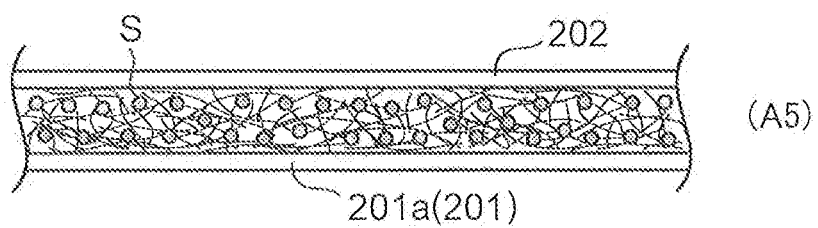

FIG. 5F is a schematic side view depicting a state just after the first sheet and the second sheet are pressure-joined.

FIG. 6 is a schematic configuration diagram depicting a powder-containing article manufacturing apparatus according to a second embodiment of the present invention.

Figure 7:
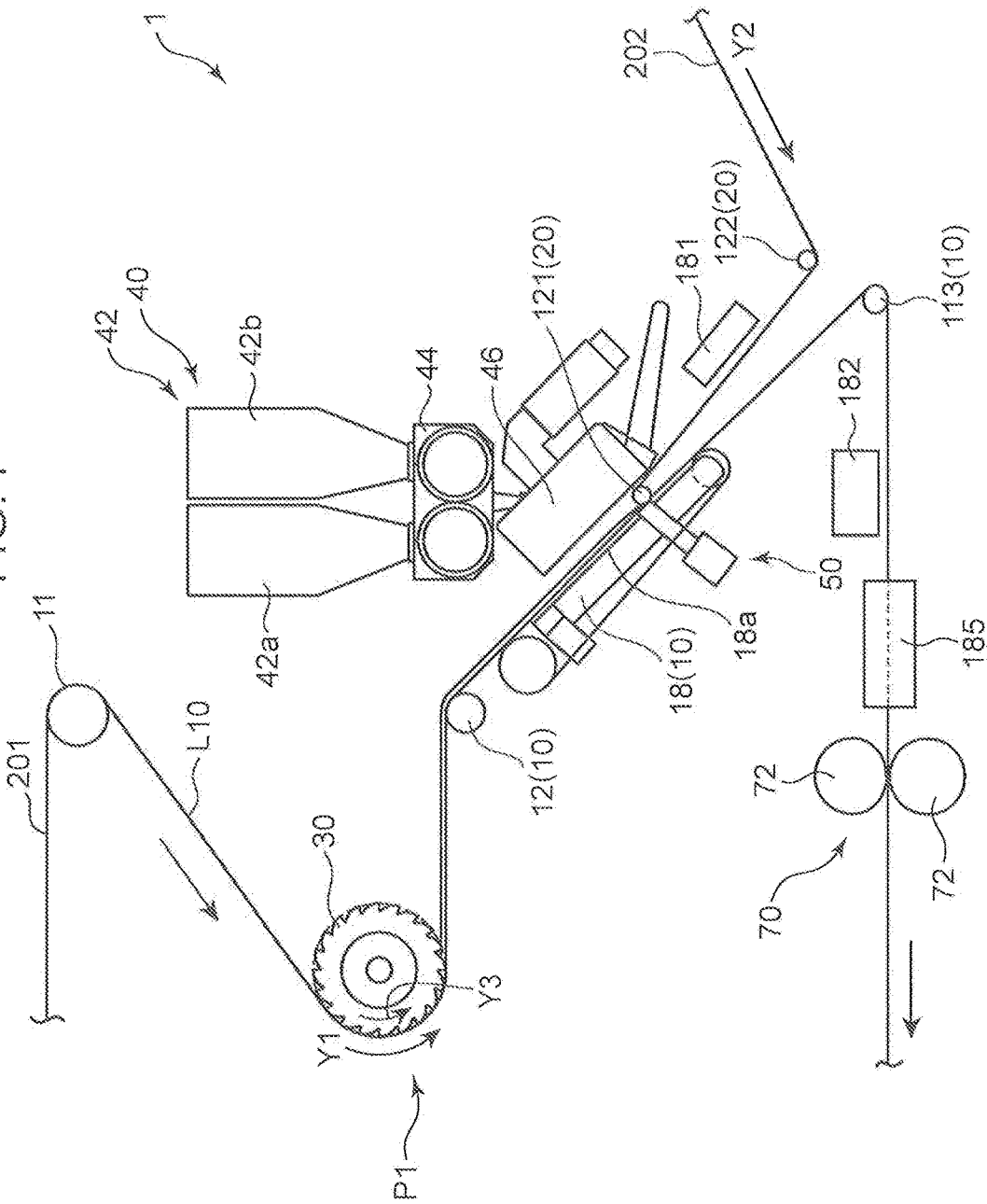

FIG. 7 is a schematic configuration diagram depicting a powder-containing article manufacturing apparatus according to a third embodiment of the present invention.

Figure 8:
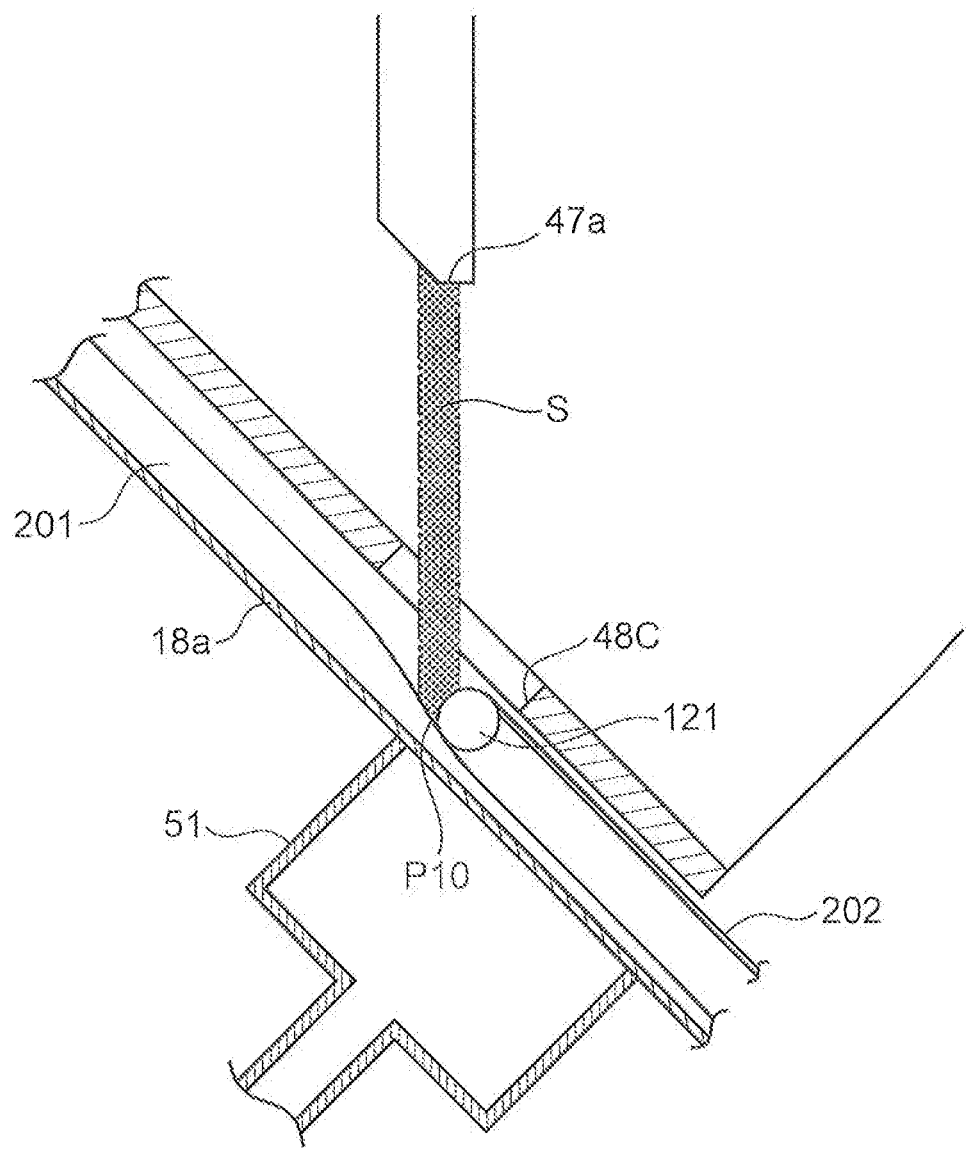

FIG. 8 is a diagram enlargedly depicting a part of FIG. 7.

DESCRIPTION OF EMBODIMENTS

With reference to the accompanying drawings, embodiments of the present invention will now be described. It should be understood that the following embodiments are specific examples of the present invention, and are not intended to restrict a technical scope of the present invention.

(1) First Embodiment

Figure 1:
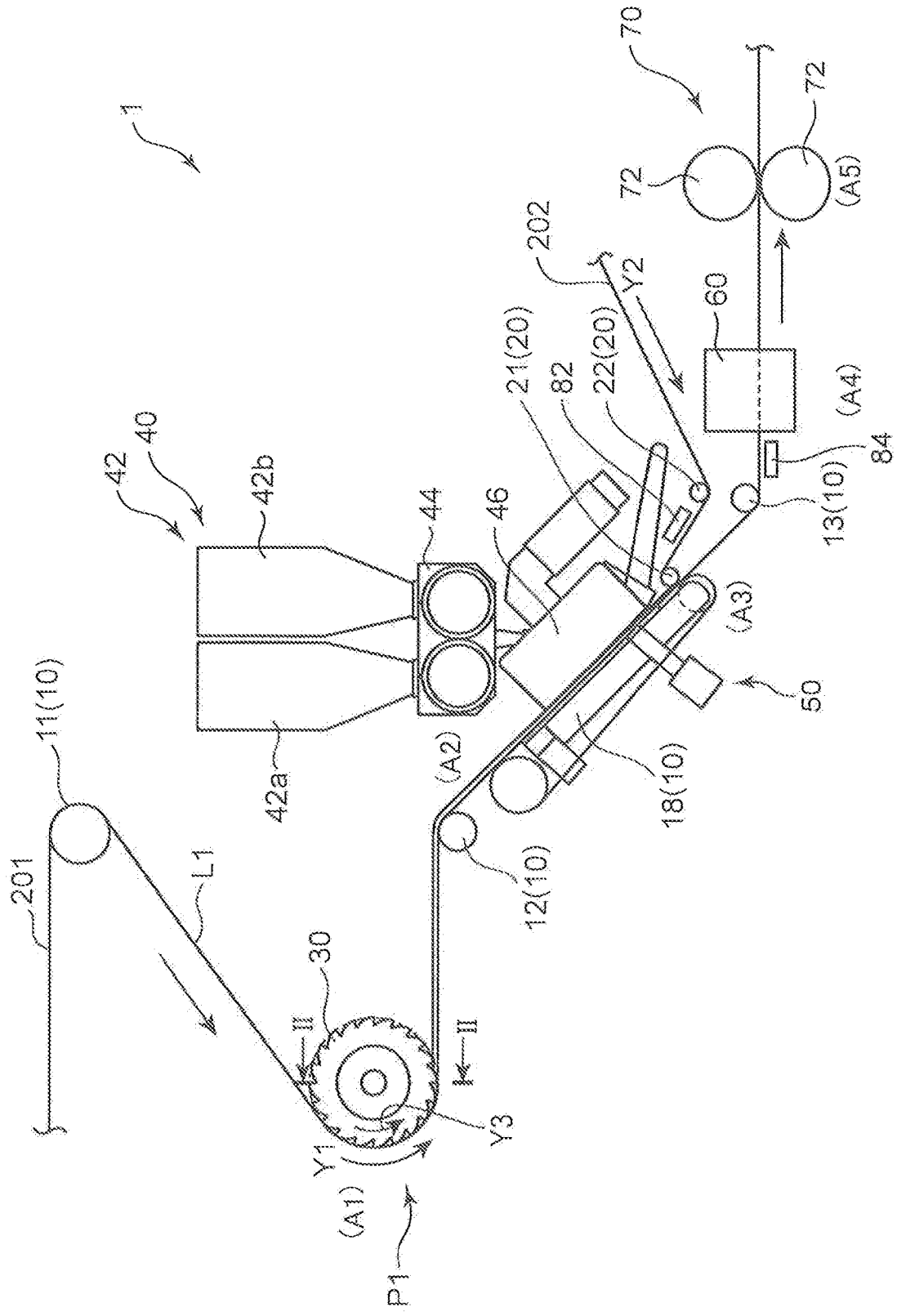
FIG. 1 is a schematic configuration diagram depicting a powder-containing article manufacturing apparatus according to a first embodiment of the present invention.

FIG. 1 is a schematic diagram depicting a powder-containing article manufacturing apparatus 1 according to a first embodiment of the present invention (hereinafter referred to simply as "manufacturing apparatus 1"). As depicted in FIG. 1, this manufacturing apparatus 1 comprises a first sheet conveyance device (sheet conveyance device) 10, a second sheet conveyance device 20, a fiber-raising device 30, a powder supply device 40, a suction device 50, a folding device 60, a pressure joining device 70, a first adhesive application device 82, and a second adhesive application device 84.

The manufacturing apparatus 1 is an apparatus for manufacturing a powder-containing article 2 containing a powder S. This embodiment will be described based on an example in which an article containing a liquid-absorbable powder S is manufactured as the powder-containing article. For example, this powder-containing article containing the liquid absorbable powder S is utilized as an absorbent body of a disposable diaper, or the like.

As depicted in FIG. 5F, the powder-containing article 2 comprises a first sheet (non-woven fabric-containing sheet) 201, a second sheet 202, and the powder S.

Examples of the powder S include a powder of SAP (Super Absorbent Polymer).

In this embodiment, as the first sheet 201, a laminate sheet with a non-woven fabric, more specifically, a sheet is used which comprises a diffusive sub-sheet 201a composing a reverse surface thereof, and a short fiber sub-sheet 201b composing a portion of the sheet on its obverse side with respect to the diffusive sub-sheet 201a, as depicted in FIG. 5A.

The short fiber sub-sheet 201b is a non-woven fabric composed of short fibers. For example, the short fiber sub-sheet 201b is a non-woven fabric obtained through air-through processing, i.e., a non-woven fabric formed by laying short fibers and applying hot air thereto.

As used in this specification, the term "short fiber" means a fiber having a fiber length of less than 100 mm, preferably less than 80 mm, more preferably less than 70 mm, as measured by the average fiber length measurement method (C method) defined in JIS 1015.

In this embodiment, as the short fiber sub-sheet 201b, a sheet composed of short fibers having an average fiber length of about 50 mm is used.

The diffusive sub-sheet 201a is a sheet having a thickness less than that of the short fiber sub-sheet 201b and a density greater than that of of the short fiber sub-sheet 201b, and having high liquid diffusivity enough to allow permeation of liquid in a wider range.

In this embodiment, as the second sheet 202, a tissue paper sheet having a thickness less than that of the first sheet 201 is used.

(1) Conveyancer Devices

The first sheet conveyance device 10 is a device for conveying the first sheet 201. The first sheet conveyance device 10 comprises a belt conveyer 18, and a plurality of guide rolls 11, 12, 13. In the first sheet conveyance device 10, the belt conveyer 18 is configured to be driven by a motor or the like, so as to convey the first sheet 201 in the direction indicated by the arrowed line Y1 in FIG. 1 along a conveyance path L1, and sequentially feed the first sheet 201 to the fiber-raising device 30, the powder supply device 40, the second adhesive application device 84, the folding device 60 and the pressure-joining device 70, in this order.

The second sheet conveyance device 20 is a device for conveying the second sheet 202. The second sheet conveyance device 20 is configured to convey the second sheet 202 toward an obverse surface of the first sheet 201 being conveyed, as indicated by the arrowed line Y2 in FIG. 1. The second sheet conveyance device 20 comprises a motor (not depicted) for feeding out the second sheet 202, and a plurality of guide rolls 21, 22 for guiding the second sheet 202 to the obverse surface of the first sheet 201.

One 21 of the guide rolls functions as a second sheet supply section for supplying the second sheet 202 to the obverse surface of the first sheet 201. Specifically, the guide roll 21 is located adjacent to the obverse surface of the first sheet 201, and the second sheet 202 is guided to the obverse surface of the first sheet 201 by the guide roll 21.

In this embodiment, the guide roll 21 is disposed at a position immediately downstream of a position opposed to an aftermentioned distribution port 48c of the powder supply device 40, i.e., at a position immediately downstream (in the conveyance direction Y1 of the first sheet 201) of a powder supply zone of the first sheet 201 to which the powder S is to be supplied. Thus, the guide roll 21 is operable to supply the second sheet 202 to the obverse surface of the first sheet 201 at a position immediately downstream (in the conveyance direction Y1 of the first sheet 201) of a powder supply position where the powder S is supplied to the first sheet 201, and cover the obverse surface of the first sheet 201 with the second sheet 202.

The first adhesive application device 82 is disposed on a conveyance path of the second sheet 202 at a position upstream of the guide roll 21 in the conveyance direction of the second sheet 202. In this embodiment, the first adhesive application device 82 is disposed at a position immediately upstream of the guide roll 21.

(ii)) Fiber-Raising Device

The fiber-raising device 30 is a device or raising fibers of e first sheet 201 from an obverse side of the first sheet 201.

Figure 2:
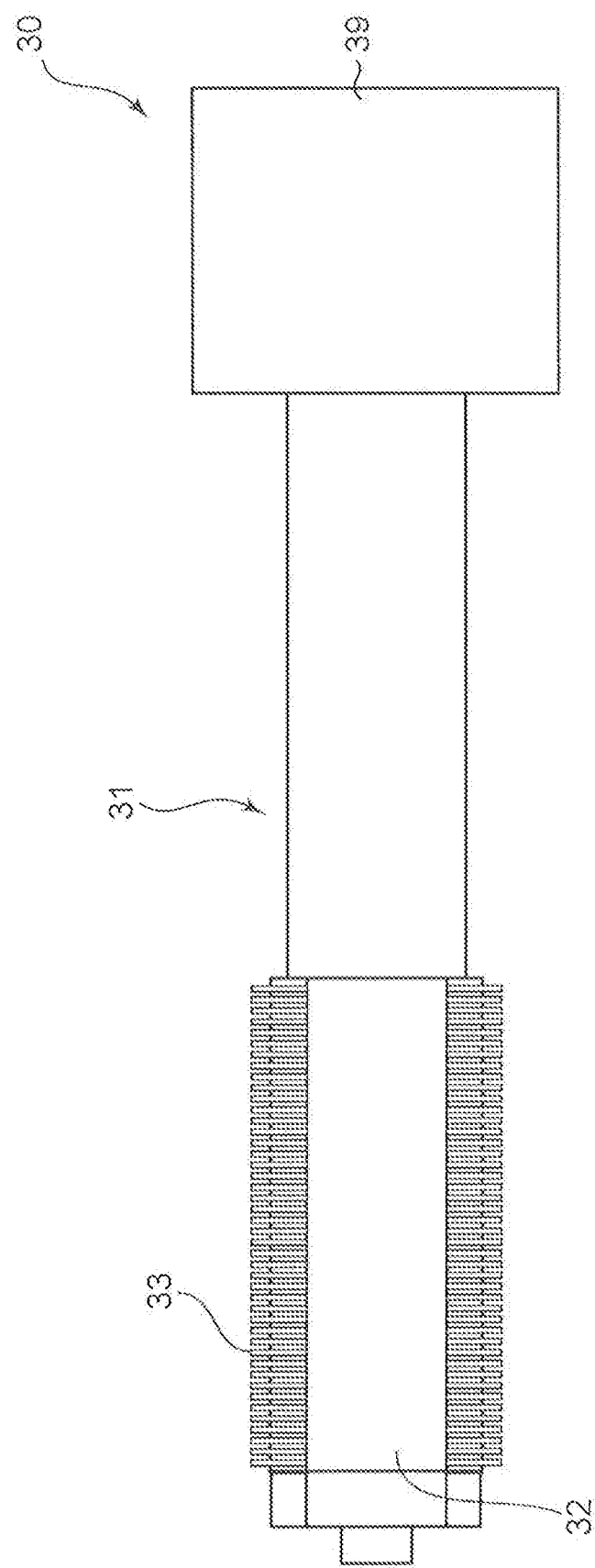
FIG. 2 is a sectional view taken along the line II-II in FIG. 1.

FIG. 2 is a sectional view taken along the line II-II in FIG. 1. The fiber-raising device 30 comprises a tiller 31, and a motor (drive section) 39 for driving the tiller 31. The tiller 31 comprises a cylindrical shaft 32 extending in a given direction, and a plurality of cutter plates 33 each fixed to an outer peripheral surface of the shaft 32. The cutter plates 33 are arranged at even intervals along a direction parallel to a center line of the shaft 32.

Figure 3:
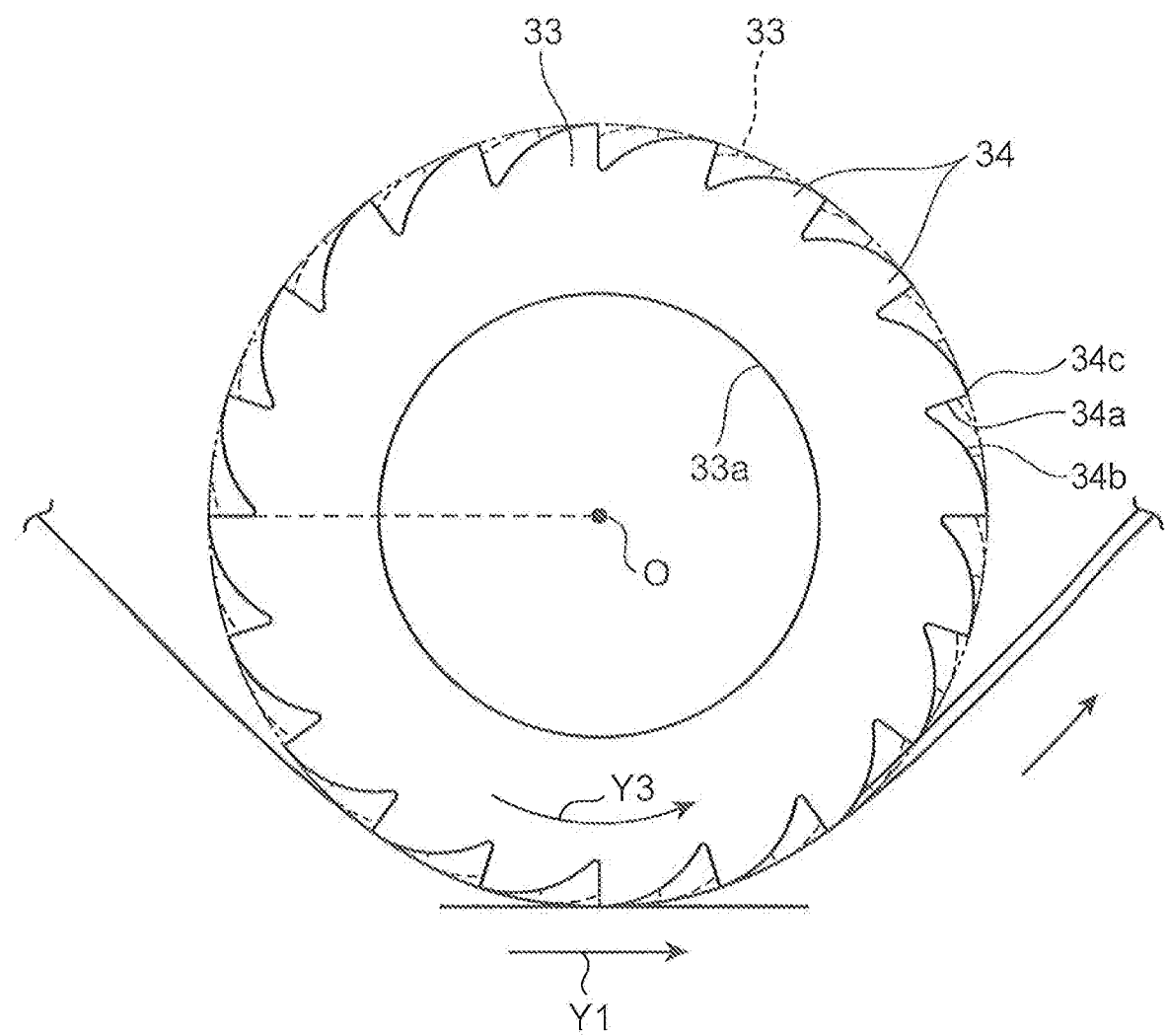
FIG. 3 is a diagram enlargedly depicting a cutter plate.

FIG. 3 is a schematic front view of the cutter plates 33. All of the cutter plates 33 have the same shape. Specifically, they have an approximately circular disk shape formed with a through-holes 33a in a central region thereof, Each of the cutter plates 33 is fixed to the outer peripheral surface of the shaft 32 in a state in which the shaft 32 is inserted in the through-hole 33a of the cutter plate 33. Each of the cutter plates 33 is fixed such that the center thereof is located on the center line O of the shaft 32.

A plurality of blades 34 are formed in an outer peripheral face of the cutter plate 33 along a circumferential direction of the cutter plate 33. All of the blades 34 have the same shape, and are arranged at even intervals in the circumferential direction of the cutter plate 33

The shaft 32 configured to be rotationally driven about the center line O of the shaft 32 by the motor 39. Upon this rotational driving, each of the cutter plates 33 is rotated about the center line O of the shaft 32 together with the shaft 32, so that the blades 34 are moved on a circumferential plane of a circular cylinder having a center line coincident with the center line O of the shaft 32.

The tiller 31 is disposed in, a posture where the center line O of the shaft 32 extends in a direction which is orthogonal to a direction parallel to the conveyance direction Y1 of the first sheet 201, and parallel to the obverse surface of the first sheet 201. Thus, the blades 34 are rotated along a circumferential plane of a circular cylinder having a center line which is a line O (center line O of the shaft 32) extending in a direction orthogonal to the conveyance direction of the first sheet 201 and parallel to the obverse surface of the first sheet 201.

The broken line in FIG. 3 indicates another cutter plate 33 disposed adjacent to the cutter plate 33 indicated by the solid line. As depicted in FIG. 3, the adjacent two cutter plates 33 are arranged in a state in which they are shifted in phase such that each of the blades 34 of one of the cutter plates 33 is located in the middle between adjacent ones of the blades 34 of the other cutter plate 33, in front view.

The fiber-raising device 30 is disposed at a position enabling the blades 34 to sequentially contact the short fiber sub-sheet 201b. Specifically, the fiber-raising device 30 is disposed such that the first sheet 201 is wound around part of an outer peripheral surface of the tiller 31 formed by distal edges 34c of the blades 34 of the cutter plates 33, in a posture where the obverse surface of the first sheet 201 (an obverse surface of the short fiber sub-sheet 201b) is oriented toward the tiller 31. In other words, the first sheet conveyance device 10 conveys the first sheet 201 in a state in which the first sheet 201 is wound around part of the outer peripheral surface of the tiller 31, and the short fiber sub-sheet 201b of the first sheet 201 is in contact with some of the distal edges 34c of the blades 34 of the cutter plates 33. In this embodiment, the first sheet 201 contacts some of the blades 34 over a given circumferential range of the cutter plates 33.

At a fiber-raising position, i.e., a position P1 where the first sheet 201 contacts some of the blades 34, a movement direction (conveyance direction) Y1 of the first sheet 201 and a movement direction Y3 of the blades 34 are set to be the same, i.e., the blades 34 are moved toward a downstream side of the conveyance direction Y1 of the first sheet 201. However, a movement speed of the blades 34 and a conveyance speed of the first sheet 201 are different from each other, i.e., the first sheet 201 is moved relative to the blades 34. Accordingly, the blades 34 sequentially scratch the first sheet 201 and thus fibers of the first sheet 201 are raised. In this embodiment, during the scratching, each of the blades 34 directly contacts only the obverse surface of the first sheet 201. However, by scratching this surface region, fibers in a given region of the first sheet 201 on its reverse side are also raised, so that almost all fibers of the short fiber sub-sheet 201b can be raised in a thickness direction of the first sheet 201. On the other hand, the diffusive sub-sheet 201a is not subjected to fiber-raising.

In this embodiment, a circumferential movement speed of the distal edges of the blades 34, i.e., a circumferential speed of the tiller 31, at the fiber-raising position P1, is set to be less than the conveyance speed of the first sheet 201. Thus, the first sheet 201 is moved relative to the blades 34, toward a downstream side of the movement direction Y3 of the blades 34 (conveyance direction Y1 of the first sheet 201). In this embodiment, the circumferential speed of the tiller 31 is set in the range of 40% to 80% of the conveyance speed of the first sheet 201. Specifically, if the circumferential speed of the tiller 31 is set to be greater than 80% of the conveyance speed of the first sheet 201, the relative movement of the first sheet 201 with respect to the blades 34 is likely to become excessively small, thereby leading to a problem of failing to sufficiently raise fiber of the first sheet 201. On the other hand, if the circumferential speed of the tiller 31 is set to be less than 40% of the conveyance speed of the first sheet 201, each of the blades 34 is likely to be excessively engaged with the first sheet 201, thereby leading to a problem of damage to the first sheet 201. Therefore, in this embodiment, the circumferential speed of the tiller 31 is set in the range of 40% to 80%, e.g., at about 55%, of the conveyance speed of the first sheet 201.

Each of the blades 34 has a first face 34a provided on an upstream side of the movement direction of the blades 34 and facing an upstream side of the conveyance direction Y1 of the first sheet 201, and a second face 34b extending from the distal edge 34c of the first face 34a (an outer edge of the first face 34a in a radial direction of the cutter plate 33) toward the downstream side of the movement direction of the blades 34 and an inward side of the radial direction of the cutter plate 33. In this embodiment, the first face 34a extends in the radial direction of the cutter plate 33 and along a line passing through the center line O of the shaft 32. Further, the second face 34b extends from the distal edge 34c of the first surface 34a toward a downstream side of a rotational direction of the cutter plate 33, while curving inwardly in the radial direction of the cutter plate 33.

The first sheet 201 is moved relative to the blades 34, toward the downstream side of the movement direction Y3 of the blades 34 (conveyance direction Y1 of the first sheet 201), as mentioned above. Therefore, the first face 34a of the blade 34 can scratch the first sheet 201 to thereby raise fibers of the first sheet 201. More specifically, the first face 34a of the blade 34 scoopingly scratches fibers of the first sheet 201 to thereby raise the fibers of the first sheet 201.

In this embodiment, the cutter plates 33 are provided in a position opposed to the entire region of the first sheet 201 in its width direction, so that fibers of the first sheet 201 (short fiber sub-sheet 201b) are raised over the entire region in the width direction thereof. Further, the cutter plates 33 are continuously rotated, so that fibers of the first sheet 201 (short fiber sub-sheet 201b) are raised over the entire region in a longitudinal direction (conveyance direction) of the first sheet 201.

Here, the first faces 34a of the blades 34 of the cutter plates 33 may be configured such that all of them extend along the radial line passing through the center line O of the shaft 32, i.e., extend in a direction orthogonal to the conveyance direction Y1 of the first sheet 201. Alternatively, some of the first faces 34a may be formed in a shape extending in a direction oblique to the conveyance direction Y1 of the first sheet 201, i.e., formed such that each of the blades 34 thereof has a knife-like blade edge. For example, the first type of cutter plate 33 with the blades 34 each having the first face 34a extending in a direction orthogonal to the conveyance direction Y1 of the first sheet 201, and the second type of cutter plate 33 with the blades 34 each having the first face 34a extending in a direction oblique to the conveyance direction Y1 of the first sheet 201, may be alternately disposed in a direction parallel to the center line of the shaft 32. Alternatively, each of the cutter plates 33 may be configured such that the first faces 34a of some of the blades 34 thereof have a shape extending in a direction orthogonal to the conveyance direction Y1 of the first sheet 201, and the first faces 34a of the remaining blades 34 have a shape extending in a direction oblique to the conveyance direction Y1 of the first sheet 201. By employing these configurations, fibers of the first plate 201 can be raised by the cutter plates 33, and fibers in the obverse surface of the first sheet 201 are partly cut by the blades 34 each having the knife-like blade edge to be made openings in the obverse surface of the first sheet 201. Thus, in operation of distributing the powder S over the obverse surface of the first sheet 201, it is possible to efficiently introduce the powder S to the inside of the first sheet 201, as described later.

FIG. 5A is a view depicting, the first sheet 201 before the fiber-raising, and FIG. 5B is a view depicting the first sheet 201 just after the fiber-raising. As depicted in FIG. 5A, before the fiber-raising, short fibers of the short fiber sub-sheet 201b are in a state in which they extend along the obverse surface of the first sheet 201, i.e., in a state in which they lie along the obverse surface of the first sheet 201. When the blades 34 of the cutter plates sequentially come into contact with the first sheet 201 in the above initial state, the blades 34 pull out the fibers of the short fiber sub-sheet 201b toward the obverse side of the first sheet 201 (toward the side of the tiller 31), and accordingly the fibers reach a state in which the fibers extend toward the obverse side of the first sheet 201, as depicted in FIG. 5B. In this state, the thickness of the first sheet 201 (short fiber sub-sheet 201b) is increased, and the density of the first sheet 201 (short fiber sub-sheet 201b) is reduced.

(iii) Powder Supply Device

The powder supply device 40 is a device for supplying the powder S from the obverse side of the first sheet 201 to the first sheet 201.

Figure 4:
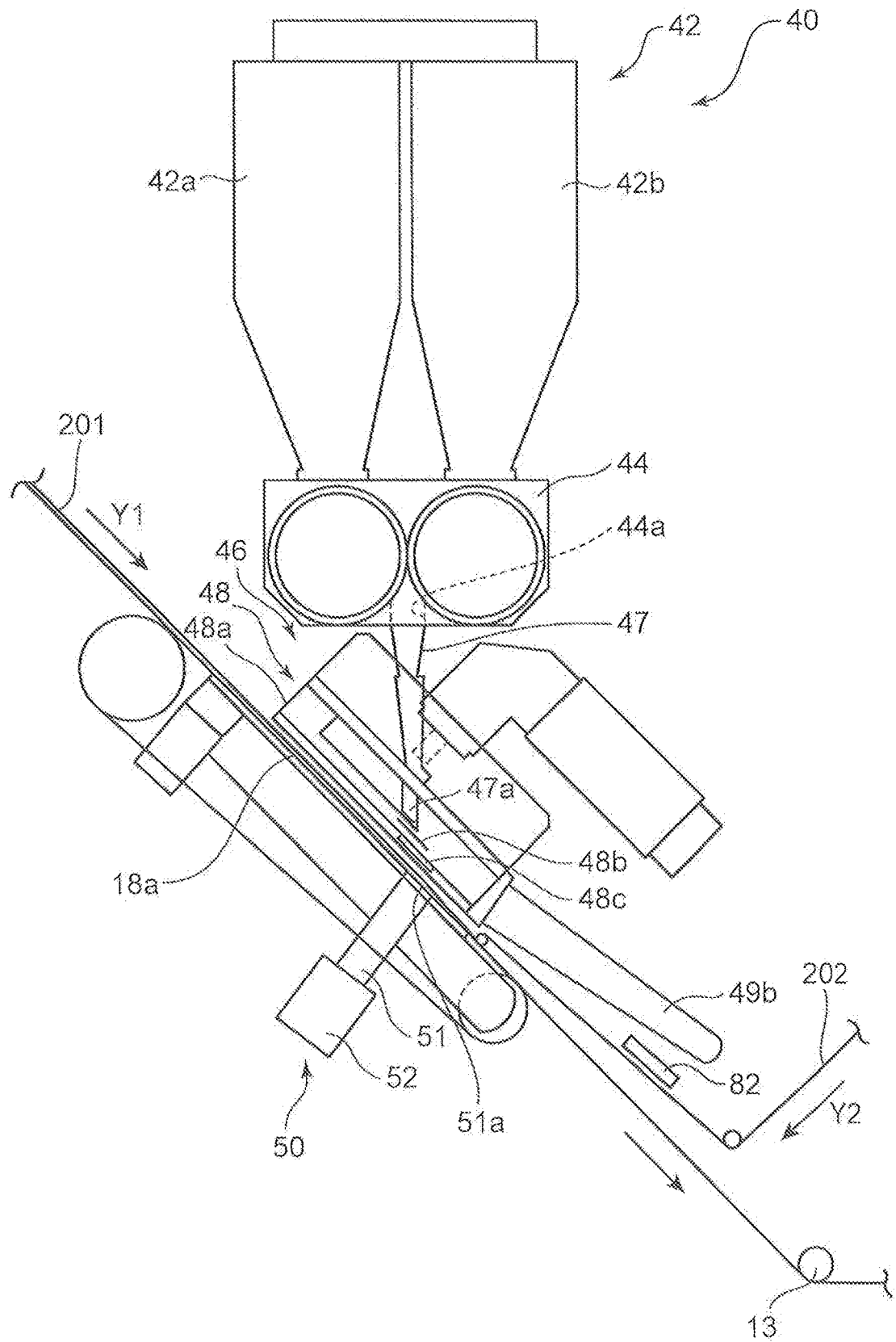
FIG. 4 is a diagram enlargedly depicting a part of FIG. 1.

The powder supply device 40 comprises a powder storage unit 42, a metering unit 44, and a powder distribution unit 46. FIG. 4 is a diagram enlargedly depicting a part of FIG. 1 and depicting, an internal structure of the powder distribution unit 46. The powder distribution unit 46 comprises a powder guide section 47, and an opening-closing mechanism 48 comprising a housing 48a internally having a relatively wide space.

The powder storage unit 42 is a component storing therein the powder S. In this embodiment, as depicted in FIGS. 1 and 4, the powder storage unit 42 comprises two tanks 42a, 42b each storing therein the powder S. Each of these two tanks 42a, 42b has a bottom wall formed with an opening for allowing the powder S to drop toward the metering unit 44, so that the powder is fed to the metering unit 44 via this opening.

The metering unit 44 is a device for metering each of the powders S fed from the tanks 42a, 42b, and feeding the metered powders to the powder distribution unit 46. The metering unit 44 is configured to continuously convey the powder S fed from each of the tanks 42a, 42b, downwardly at a given flow rate. The powder S to be conveyed falls downwardly from an outlet 44a provided in a bottom wall of the metering unit 44.

The powder guide section 47 is a component for guiding the powder falling from the outlet 44a of the metering unit 44, downwardly. The powder guide section 47 is composed of a vertically-extending tubular member which is internally formed with a space communicating with the outlet 44a. The powder falling from the outlet 44a of the metering unit 44 flow through the powder guide section 47, and then fall downwardly from a powder supply port 47a formed at a lower end of the powder guide section 47.

The lower end of the powder guide section 47 formed with the powder supply port 47a is inserted into the housing 48a through a top wall of the housing 48a, so that the powder S falling from the powder supply port 47a flow into the housing 48a.

A bottom wall of the housing 48a has a distribution port 48c which is formed at a position opposed to the powder supply port 47a to penetrate the bottom wall in an upward-rearward direction. More specifically, the distribution port 48c is disposed at a position spaced apart, vertically downwardly from the powder supply port 47a, and overlapping the powder supply port 47a in top plan view (as viewed along the vertical direction). Accordingly, the powder S falling from the powder supply port 47a falls toward the distribution port 48c.

The belt conveyer 18 is disposed beneath the distribution port 48c, so that the powder S falling toward the distribution port 48c is, supplied to the first sheet 201 at a position on the belt conveyer 18, through the distribution port 48c, from the obverse side of the first sheet 201. In this embodiment, the powder S is supplied to the first sheet 201 uniformly in terms of the width direction of the first sheet 201.

As depicted in FIG. 4, the belt conveyer 18 is disposed such that a downstream end region, in the conveyance direction Y1 of the first sheet 201, of a conveyer belt 18a thereof on which the first sheet 201 is placed is located downward of an upstream end region of the conveyer belt 18a in the conveyance direction Y1 of the first sheet 201. Thus, at a position opposed to the distribution port 48c, the first sheet 201 receives supply of the powder S from above while being conveyed obliquely downwardly with respect to the vertical direction.

The housing 48a is configured such that the bottom wall thereof extends parallel to the obverse surface of a part of the first sheet 201 being conveyed on the belt conveyer 18, at a position adjacent to the obverse surface of the part of the first sheet 201, and the distribution port 48c is disposed at a position adjacent to the obverse surface of the part of the first sheet 201.

Here, the metering unit 44 continuously conveys the powder S downwardly, as mentioned above, so that the powder S continuously falls from the powder supply port 47a toward the distribution port 48c. However, in this embodiment, an aftermentioned shutter valve 48b provided in the opening-closing mechanism 48 is operable to intermittently restrict the powder S from reaching the first sheet 201. This allows the powder S to be intermittently supplied to the first sheet 201.

More specifically, the opening-closing mechanism 48 is provided with a shutter value 48b fixed to the housing 48a in a rotatable state. This shutter value 48b is configured to periodically pass through a region between the powder supply port 47a and the distribution port 48c to cover an upper side of the distribution port 48c to thereby periodically restrict the powder S from reaching the distribution port 48c. As depicted in FIG. 4, in this embodiment, the shutter valve 48b is a plate-shaped member extending, parallel to the part of the first sheet 201 being conveyed on the belt conveyer 18, wherein the shutter valve 48b is configured to be rotationally driven on a plane parallel to the part of the first sheet 201 by a motor, so as to periodically pass through the region between the powder supply port 47a and the distribution port 48c.

In this way, the shutter valve 48b periodically restricts the powder S from reaching the first sheet 201 via the distribution port 48c, so that the powder S is intermittently supplied from the distribution port 48c to the first sheet 201.

In FIG. 4, a component designated by the reference sign 49b is a discharger for discharging, to the outside, a part of the powder S within the housing 48a, scattered around the distribution port 48c when the shutter valve 48b restricts the powder S from reaching the first sheet 201.

(iv) Suction Device

The suction device 50 is a device for suctioning the part of the first sheet 201 being conveyed on the belt conveyer 18 from the reverse side of the first sheet 201.

The suction device 50 comprises a suction passage 51 formed with a suction port 51a, and a suction pump 52 connected to the suction passage 51, wherein the suction device 50 is configured to suck in air surrounding the suction port 51a by driving of the suction pump 52. The suction port 51a is disposed around a position opposed to the distribution port 48c. In this embodiment, the suction port 51a extends from a position just below the distribution port 48c to a position downstream of the distribution port 48c in the conveyance direction Y1 of the first sheet 201, so that the suction device 50 can suction the reverse surface of a part of the first sheet 201 passing through a region from the position just below the distribution port 48c to the position downstream of the distribution port 48c in the conveyance direction Y1 of the first sheet 201. More specifically, the suction port 51a is disposed on a reverse side of the conveyer belt 18a, and configured to suction the part of the first sheet 201 via a plurality of air holes formed in the conveyer belt 18a.

(v) Adhesive Application Devices and Folding Device

The first adhesive application device 82 is a device for applying an adhesive to the second sheet 202. For example, the first adhesive application device 82 may be designed to apply a hot-melt adhesive to the second sheet 202. The first adhesive application device 82 is disposed on the conveyance path of the second sheet 202 at a position upstream of the guide roll 21, as mentioned above, and configured to apply an adhesive to a surface of the second sheet 202 at a position before reaching to the obverse surface of the first sheet 201.

Accordingly, the second sheet 202 applied with the adhesive is covered over the first sheet 201 by the guide roll 21, and, during the covering, the first sheet 201 and the second sheet 202 are adhesively bonded together.

As above, in this embodiment, the guide roll 21 functions as a second sheet supply section for supplying the second sheet 202 to the obverse surface of the first sheet 201, and further functions as a bonding device for adhesively bonding the two sheets 201, 202 together.

Further, in this embodiment, the guide roll 21 is configured to pressure join the two sheets 201, 202 bonded together, in a thickness direction of them. Thus, through the guide roll 21, the first sheet 201 and the second sheet 202 are bonded together while being pressure-joined in the thickness direction of them.

The second adhesive application device 84 is located downstream of the guide roll 21 in the conveyance direction of the first sheet 201. The second adhesive application device 84 is a device for applying an adhesive to part of a region of the second sheet 202 protruding outwardly from the first sheet 201. For example, the second adhesive application device 84 may be designed to apply a hot-melt adhesive to the second sheet 202.

More specifically, in this embodiment, the second sheet 202 is composed of a sheet having a width greater than that of the first sheet 201. Thus, when the second sheet 202 is supplied and bonded to the obverse surface of the first sheet 201 through the guide roll 21, the second sheet 202 on the first sheet 201 will protrude outwardly with respect to the first sheet 201 in the width direction thereof. In this embodiment, width-directional opposite end portions of the second sheet 202 protrude outwardly with respect to the first sheet 201. In this state, the second adhesive application device 84 is operable to apply an adhesive to the width-directional opposite end portions of the second sheet 202.

The folding device 60 is a device for holding the second sheet 202 such that the second sheet 202 enfolds the first sheet 201, as depicted in FIG. 5E. More specifically, the folding device 60 is configured to fold the width-directional opposite end portions of the second sheet 202 such that it wraps around the reverse side of the first sheet 201 to extend along the reverse surface of the first sheet 201.

Here the folding device 60 is located downstream of the second adhesive application device 84 in the conveyance direction of the first sheet 201. In this embodiment, the folding device 60 is located immediately downstream of the second adhesive application device 84.

Thus, when the width-directional opposite end portions of the second sheet 202 applied with the adhesive by the second adhesive application device 84 are folded by the folding device 60, they are bonded to the reverse surface of the first sheet 201.

As above, in this embodiment, the folding device 60 also functions as a bonding device for adhesively bonding the first sheet 201 and the second sheet 202 together.

(vi) Pressure-Joining Device

The pressure joining device 70 is a device for pre sure-joining an assembly of the first sheet 201 and the second sheet 202 bonded together, in a thickness direction thereof. In this embodiment, the pressure-joining device 70 comprises a pair of rollers 72, 72, wherein the pressure joining device 70 is configured to allow the assembly of the first sheet 201 and the second sheet 202 to pass through between the rollers 72, 72 so as to pressure-join the assembly in the thickness direction thereof.

(vii) Manufacturing Method

A method for manufacturing a powder-containing article 2 containing a powder S, by the manufacturing apparatus 1 configured as described above is as follows.

First of all, a first sheet 201 is prepared in which a portion thereof to be subjected to fiber-raising in an aftermentioned fiber-raising step, i.e., a portion thereof exposed to an obverse side of the first sheet 201 is composed of a short fiber sub-sheet 201b comprised of a non-woven fabric of short fibers (preparation step). Subsequently, the first sheet 201 is conveyed along a conveyance path L1 (conveyance step).

Subsequently, the first sheet 201 is subjected to fiber-raining using the fiber-raising device 30 to thereby shift the state of the first sheet 201 from the state depicted in FIG. 5A to the state depicted in FIG. 5B (fiber-raising step A1).

Subsequently, the powder S is supplied from the powder supply device 40 to the first sheet 201 from the obverse side thereof, and introduced to and held in the inside of the first sheet 201, to thereby shift the state of the first sheet 201 from the state depicted in FIG. 5B to the state depicted in FIG. 5C (powder supply step A2). In this embodiment, during the powder supply step, the powder S is supplied to the first sheet 201 from the obverse side thereof while the first sheet 201 is suctioned from a reverse side thereof by the suction device 50.

Subsequently, through the guide roll 21, a second sheet 202 is supplied to an obverse surface of the first sheet 201 after being supplied with the powder S (second sheet supplying step A3). During the second sheet supplying step, after an adhesive is applied onto the second sheet 202 by the first adhesive application device 82, the second sheet 202 is supplied to the obverse surface of the first sheet 201. Further, through the guide roll 21, the first sheet 201 and the second sheet 202 are bonded together while pressure-joining them in their thickness direction, to thereby shift the state of the first sheet 201 from the state depicted in FIG. 5C to the state depicted in FIG. 5D (first bonding step A3, bonding step).

Subsequently, after an adhesive is applied onto the supplied second sheet 202 by the second adhesive application device 84, the second sheet 202 is folded to bond the two sheets 201, 202 together, by the folding device 60, to thereby shift the state of an assembly of the two sheets 201, 202 from the state depicted in FIG. 5D to the state depicted in FIG. 5E (second bonding step A4, bonding step).

Last of all, the assembly of the first sheet 201 and the second sheet 202 bonded together is pressure joined in a thickness direction thereof by the pressure joining device 70, to thereby shift the state of the assembly of the two sheets 201, 202 from the state depicted in FIG. SE to the state depicted in FIG. SF (pressure joining step A5) to manufacture a powder-containing article 2 containing a liquid-absorbable powder S. The powder S is, intermittently supplied from the powder supply device 40 in the conveyance direction of the first sheet 201, as mentioned above. Thus, after passing through the pressure joining device 70, the powder-containing article 2 is appropriately cut in a zone thereof in which the powder S is not placed, and used as an absorbent body of a diaper, or the like.

(viii) Functions, etc.

As above, in the manufacturing apparatus 1 and the powder-containing article manufacturing method according to the first embodiment, before supplying the powder S to the first sheet 201, fibers of the short fiber sub-sheet 201b of the first sheet 201 exposed to the obverse surface thereof are raised from the obverse side thereof.

Thus, the powder S supplied to the first sheet 201 from the obverse side thereof is introduced into the first sheet 201, so that it is possible to manufacture a powder-containing article 2 in which particles of the powder S are moderately dispersed and stably disposed at adequate positions.

More specifically, in a state in which the first sheet 201 comprised of a non-woven fabric has not yet been subjected to fiber-raising, fibers of the first sheet 201 extend along the obverse surface of the first sheet 201 while being superimposed on each other in the thickness direction of the first sheet 201, as depicted in FIG. 5A. For this reason, when the powder S is supplied to the obverse surface of the first sheet 201 in the above state, the powder S is merely placed on the obverse surface of the first sheet 201 without being introduced to the inside of the first sheet 201. Thus, even after covering the powder S on the first sheet 201 by the second sheet 202, particles of the powder S can be freely moved between the two sheets 201, 202 along the obverse surface of the first sheet 201, so that positions of the particles of the powder S are unstable. Therefore, there is a possibility that a user has an uncomfortable feeling, or a possibility that desired performance such as liquid-absorbability cannot be sufficiently obtained, as with the powder-containing article manufactured by the apparatus disclosed in the WO 2014/104118A. Moreover, due to positional bias, particles of the powder S come into contact with each other, Thus, in the case where the powder S has liquid absorbability, a phenomenon occurs that, when absorbing liquid during use, one of two particles of the powder S in contact with each other restricts expansion of the other particle, so called "gel block", leading to deterioration in liquid-absorbability of the powder-containing article 2.

Compared with this, in the first embodiment, by raising fibers of the first sheet 201, spaces are formed between respective ones of fibers composing the first sheet 201 (short fiber sub-sheet 201b), and particles of the powder S supplied to the first sheet 201 (short fiber sub-sheet 201b) are introduced into the spaces (inter-fiber spaces). Therefore, it is possible to interpose one or more fibers between adjacent ones of the particles of the powder S to restrict displacement of the particles of the powder S by the fibers. Therefore, it is possible to manufacture a powder-containing article 2 in which particles of the powder S are moderately dispersed and adequately and, stably disposed at desired positions. Further, in a powder-containing article 2 containing a liquid-absorbable powder S, it is possible to suppress displacement or positional bias of the liquid-absorbable powder 5, and occurrence of the gel block, to enhance liquid absorbability.

The first sheet 201 (short fiber sub-sheet 201b) becomes soft as a result of the fiber-raising, and has an excellent cushioning function, so that it is possible to suppress a situation where, when the powder S is supplied to the first sheet 201, some particles of the supplied powder S bounce from and drop out of the first sheet 201. Therefore, it is possible to efficiently supply the powder S to the first sheet 201.

Particularly in the first embodiment, the powder S is supplied from the obverse side of the first sheet 201 while the first sheet 201 is suctioned from the reverse side thereof by the suction device 50. Thus, particles of the powder S can be dispersedly arranged within the first sheet 201 (short fiber sub-sheet 201b) in the thickness direction of the first sheet 201. Therefore, the particles of the powder S can bury, respectively, in the inter-fiber spaces, so that it is possible to more reliably interpose one or more fibers between adjacent ones of the particles of the powder S.

Further, the suction port 51a of the suction device 50 is provided between the position beneath the distribution port 48c, i.e., the position opposed to the distribution port 48c, and the positon downstream of the distribution port 48c in the conveyance direction Y1 of the first sheet 201, to thereby suppress a situation where a suction force by the suction device 50 is given to the first sheet 201 at a position before reaching the powder supply position. Therefore, a situation can be suppressed in which raised fibers lie down due to the suction force before supplying the powder S, so that it is possible to form spaces between respective ones of the fibers to reliably introduce particles of the powder S into the inter-fiber spaces.

Here, only fibers of the short fiber sub-sheet 201b in the first sheet 201 are raised, and the diffusive sub-sheet 201a composing the reverse surface and its adjacent portion of the first sheet 201 is not subjected to fiber-raising. Thus, the density of the reverse surface and its adjacent portion of the first sheet 201 can be maintained at a higher value than that of the remaining portion on the obverse side of the first sheet 201, so that it is possible to suppress a situation where the powder S escapes through the reverse side of the first sheet 201, while allowing particles of the powder S to be introduced to the inside of the first sheet 201 from the obverse side thereof and moderately dispersed, as mentioned above, and thus efficiently dispersedly arrange the particles of the powder S within the first sheet 201. Particularly, in this embodiment, the reverse surface of the first sheet 201 is composed of the diffusive sib-sheet 201b having a relatively high density, and this diffusive sib-sheet 201b is maintained in the high density state without being subjected to fiber-raising. Therefore, it is possible to more reliably restrict the powder S from escaping toward the reverse side of the first sheet 201, by the diffusive sub-sheet 201b.

In the first embodiment, fibers composing a portion of the first sheet 201 to be subjected to fiber-rising are short fibers. Thus, upon being subjected to fiber-raising, distal ends of raised fibers of the first sheet 201 are more exposed to the obverse side of the first sheet 201, so that many of spaces formed between respective ones of the fibers (inter-fiber spaces) can be opened on the obverse side of the first sheet 201. Therefore, it is possible to allow particles of the powder S to more reliably flow into the inter-fiber spaces through the openings around the distal ends of the raised fibers.

It is to be understood that a portion of the first sheer to be subjected to fiber-raising may be comprised of a non-woven fabric composed of long fibers. In this case, the fibers can also be pulled out toward the obverse side of the first sheet 201 by fiber-raising so as to form spaces between respective ones of the fibers of the first sheet 201. However, in this case, as compared to the case using the no-wove fabric of short fibers, a frequency that an inter-fiber space is opened on the obverse side of the first sheet is kept down, and thereby the powder S is less likely to be introduced to the inside of the first sheet. For this reason, in this case, the fiber-raising device needs to be designed to have a structure suited to a non-woven fabric of long, fibers, or needs to be operated under operation conditions suited to a non-woven fabric of long fibers.

Compared with this, in the first embodiment, the obverse side of the first sheet 201 is comprised of a non-woven fabric of short fibers, so that fiber-raising can be easily achieved by the fiber-raising device 30 configured as described above, and, through the fiber-raising, it is possible to obtain a state in which distal ends of many of the fibers are exposed to the obverse side of the first sheet 201. Therefore, particles of the powder S are allowed to move to the inside of the first sheet 201 via openings around the distal ends of the fibers, i.e., can be more reliably introduced into the inter-fiber spaces.

In the first embodiment, the first sheet 201 and the second sheet 202 are bonded together by the guide roll 21 and the folding device 60. Thus, the powder S in the first, sheet 201 can be confined therein by the second sheet 202, so that it is possible to avoid leakage of the powder S from between the first sheet 201 and the second sheet 202. Therefore, the powder S can be adequately contained in the powder-containing article 2. Particularly, through the guide roll 21, the second sheet 202 is supplied to and bonded to the obverse surface of the first sheet 201, in the vicinity of the powder supply position where the powder S is supplied to the first sheet 201. Thus, it is possible to more reliably suppress leakage of the powder S from the first sheet 201. Further, by the folding device 60, the first sheet 201 and the second sheet 202 are bonded together in a state in which the width-directional opposite end portions of the second sheet 202 enfolds the first sheet 201. Thus, it is possible to suppress leakage of the powder S from width directional opposite ends and others of the first sheet 201.

In the first embodiment, the first sheet 201 and the second sheet 202 are pressure-joined by the pressure-joining device 70. Thus, it is possible to keep down the thickness of the powder-containing article 2. Further, by keeping down the thickness of the powder-containing article 2, particles of the powder S can be securely pressed by surrounding fibers. Thus, it is possible to suppress displacement of the particles of the powder S in a direction along the obverse surface of the powder-containing article 2, and stably arrange the particles of the powder S at more adequate positions.

In the first embodiment, at the fiber-raising position P1., the blades 34 are moved from the upstream side to the downstream side of the conveyance direction Y1 of the first sheet 201 under the condition that the movement direction Y3 of the blades 34 is coincident with the movement direction Y1 of the first sheet 201. Further, the movement speed of the blades 34 is set to be less than the movement (conveyance) speed of the first sheet 201.

Thus, it is possible to increase the conveyance speed of the first sheet 201 to enhance efficiency regarding manufacturing of the powder-containing article 2, and keep down the relative speed between the first sheet 201 and the blades 34, to suppress a situation where the first sheet 201 is excessively engaged with each of the blades 34, leading to damage to the first sheet 201, and a situation where, due to such excessive engagement, the conveyance speed of the first sheet 201 largely fluctuates, and thus convey the first sheet 201 toward the downstream sided, in an adequate state and at an adequate speed.

Specifically, when the blades 34 are moved in a direction opposite to the conveyance direction Y1 of the first sheet 201, at the fiber-raising position P1, i.e., the blades 34 are moved from the downstream side to the upstream side of the conveyance direction Y1 of the first sheet 201, under the condition that the conveyance speed of the first sheet 201 is increased, the movement speed of the first sheet 201 becomes extremely high, relative to the movement speed of the blades 34. Thus, when they come into contact with each other, the first sheet 201 is likely to be excessively engaged with each of the blades 34.

Compared with this, in the first embodiment, the movement direction Y3 of the blades 34 and the conveyance direction Y1 of the first sheet 201 are the same at the fiber-raising position P1, so that it is possible to keep down the relative speed therebetween to thereby suppress the situation where the first sheet 201 is excessively engaged with each of the blades 34.

Here, even if, under the condition that the movement direction Y3 of the blades 34 is set to be the same as the conveyance direction Y1 of the first sheet 201, and the movement speed of the blades 34 is set to be greater than the conveyance speed of the first sheet 201, the first sheet 201 is moved relative to the blades 34, from the downstream side to the upstream side of the movement direction of the blades 34, it is possible to bring the first sheet 201 into contact with a portion of each of the blades 34 on the downstream side of the movement direction of the blades 34 to raise fibers of the first sheet 201. In this case, however, it is necessary to move the blades 34 at a relatively high speed, and fibers of the first sheet 201 are less likely to be raised, because when each of the blades 34 comes into contact with the obverse surface of the first sheet 201, the fibers of the first sheet 201 are pushed by the blade 34, toward the conveyance direction of the first sheet 201 in a laying manner.

Compared with this, in this embodiment, the movement direction Y3 of the blades 34 is set to be the same as the conveyance direction Y1 of the first sheet 201, and the movement speed of the blades 34 is set to be less than the conveyance speed of the first sheet 201. Thus, the obverse surface of the first sheet 201 is moderately engaged with each of the blades 34, while the conveyance speed of the first sheet 201 is maintained, at a relatively high value, so that fibers of the first sheet 201 can be successfully raised.

In this embodiment, in each of the blades 34, the first face 34a which is an upstream-side face in the movement direction of the blades 34 and faces the upstream side of the conveyance direction Y1 of the first sheet 201 at the fiber-raising position P1 extends in the radial direction of the cutter plate 33, and the second face 34b which is a downstream-side face in the movement direction of the blades 34 and faces the downstream side of the conveyance direction Y1 of the first sheet 201 at the fiber-raising position P1 extends from the outer edge 34c of the first face 34a in the radial direction of the cutter plate 33, toward the downstream side of the movement direction of the blades 34 and the inward side of the radial direction of the cutter plate 33. Accordingly, the distal edge 34c of each of the blades 34 which is a portion contactable with the first sheet 201 is formed in a shape sharp-edged toward an outward side of the radial direction of the cutter plate 33. Thus, the distal edge 34c of the blade 34 can be adequately engaged with the first sheet 201 to raise fibers of the first sheet 201.

Further, the first face 34a contactable with the sheet 201 extends in a direction orthogonal to the obverse surface of the first sheet 201, at the fiber-raising position P1. Thus, when the first sheet 201 is separated from the blade 34, fibers of the first sheet 201 are more likely to be released from the blade 34, so that it is possible to adequately convey the first sheet 201. That is, each of the blades 34 can be smoothly separated from the first sheet 201, so that it is possible to suppress a situation where the first sheet 201 is damaged due to excessive engagement between each of the blades 34 and the first sheet 201.

In this embodiment, the conveyer belt 18a of the belt conveyer 18 is disposed to extend obliquely downwardly with respect to the vertical direction, to convey the first sheet 201 obliquely downwardly at a position opposed to the distribution port 48c, Thus, both of a movement direction of the powder S falling from the distribution port 48c and the conveyance direction of the first sheet 201 can, be set to extend vertically downwardly, so that it is possible to suppress a situation where some particles of the powder S bounce from and drop out of the first sheet 201, and thus efficiently supply the powder S to the first sheet 201.

(2) Second Embodiment

Although the first embodiment has been described based on an example in which the belt conveyer 18 is used as a device for conveying the first sheet 201 to the powder distribution unit 46, a conveyance drum 518 may be used, in place of the belt conveyer 18, as depicted in FIG. 6. In this case, the first sheet 201 after being subjected to fiber-raising is supplied to an outer peripheral surface of the conveyance drum 518. Further, the powder S is supplied to the first sheet 201 at a position along the outer peripheral surface of the conveyance drum 518, and then, through the guide roll 21, the second sheet 202 is supplied to the first sheet 201 at a position along the outer peripheral surface of the conveyance drum 518. Then, between the guide roll 21 and the conveyance drum 518, the first sheet 201 and the second sheet 202 to which an adhesive is applied by the first adhesive application device 82 are bonded together while being pressure joined in the thickness direction of them. Further, a plurality of air holes may be formed in the outer peripheral surface of the conveyance drum 518, and communicated with the suction device 50 such that the first sheet 201 can be suctioned from the reverse side thereof via the air holes.

By using the conveyance drum 518 in this manner, a device size in the conveyance direction of the first sheet 201, and a device installation area can be reduced as compared to the belt conveyer 18. On the other hand, the belt conveyer 18 makes it possible to avoid a situation where centrifugal force is applied to the first sheet 201 and the powder S as in the case using the conveyance drum 518, and thus more efficiently supply the powder S to the first sheet 201.

(3) Third Embodiment

The first embodiment has been described based on an example in which the guide roll 21 of the second sheet conveyance device 20 for supplying the second sheet 202 to the obverse surface of the first sheet 201 is disposed downstream (in the conveyance direction Y1 of the first sheet 201) of the position opposed to the distribution port 48c, i.e., downstream (in the conveyance direction Y1 of the first sheet 201) of the powder supply position where the powder S is supplied to the first sheet 201. Alternatively, the guide roll 21 may be disposed as depicted in FIG. 7 and FIG. 8 in which a part of FIG. 7 is enlargedly depicted.

Specifically, in the third embodiment, as depicted in FIG. 8, one 121 of two guide rolls of a second sheet conveyance device 20 for supplying the second sheet 202 to the obverse surface of the first sheet 201 is disposed at the position opposed to the distribution port 48c, i.e., at the powder supply position where the powder S is supplied to the first sheet 201.

More specifically, in the third embodiment, the first sheet 201 is conveyed obliquely downwardly, as with the first embodiment. Accordingly, a second sheet supply position P10 where the second sheet 202 is supplied to the obverse surface of the first sheet 201 through the guide roll 121 is located upstream, in the conveyance direction of the first sheet 201, of a position vertically downward of a shaft center of the guide roll 121, and an upper side, in the vertical direction, of the second sheet supply position position P10 is opened. The distribution port 48c is disposed to face a position upward, in the vertical direction, of the second sheet supply position position P10. Thus, in the third embodiment, the powder supply position where the powder S is supplied to the first sheet 201 and the second sheet supply position P10 where the second sheet 202 is supplied to the first sheet 201 are coincident with each other, so that, at this position, the powder S is supplied to the first sheet 201, and simultaneously the second sheet 202 is supplied to the first sheet 201. Therefore, in the third embodiment, it is possible to more reliably suppress leakage of the powder S from between the two sheets 201, 202.

Further, in the third embodiment, as with the first embodiment, a first adhesive application device 181 is provided at a position upstream, in the conveyance direction of the second sheet 202, of the guide roll 121, so that, simultaneously with supply of the powder S to the first sheet 201, the first sheet 201 and the second sheet 202 are bonded together. This makes it possible to more reliably suppress the leakage of the powder S from between the two sheets 201, 202. In the third embodiment, the guide roll 121 is configured to pressure-join the first sheet 201 and the second sheet 202 in their thickness direction, in the same manner as that in the first embodiment.

In the third embodiment, the suction passage 51, the suction passage 51 extends toward the downstream side from a position just below the distribution port 48c, the powder supply position where the powder S is supplied to the first sheet 201, and applies suction to a region from the powder supply position to a position downstream of the powder supply position, in the same manner as that in the first embodiment.

In the third embodiment, a second adhesive application device 183, a folding device 185 and a pressure-joining device 70 are provided, and the first sheet 201 and the second sheet 202 are further bonded together and an assembly thereof is pressure-joined in a thickness direction thereof, in the same manner as that in the first embodiment.

(4) Modifications

As the powder S, one type of SAP powder having a single absorption property may be used, or a mixture of one type of SAP powder having a high liquid-absorbability and another type of SAP powder having a high absorption rate may be used. For example, it is conceivable that the type of SAP powder having a high liquid-absorbability and the type of SAP powder having a high absorption rate are stored, respectively, in the tank 42a and the tank 42b of the powder storage unit 42 depicted in FIG. 1, and the two type of SAP powders are fed from the two tanks 42a, 42b at a given ratio.

The powder S may be any liquid-absorbable powder other than the SAP powders. Further, the powder S is not limited to a liquid-absorbable powder. For example, as the powder S, a powder of cool sensation material or fragrance material may be used. Further, the plural types of powders may be used in combination.

A specific configuration of the first sheet 201 is not limited to the aforementioned configuration, as long as at least a given region from the obverse surface toward the reverse side of the first sheet 201 is comprised of a non-woven fabric. For example, the on-woven fabric as an obverse-side portion may be configured as a single layer or may be configured as a multilayer. A reverse-side portion may be comprised of a non-woven fabric of long fibers, such as a diffusive sub-sheet, or may be a non-woven fabric of short fibers, or a synthetic resin sheet. In the first embodiment, the "given region from the obverse surface toward the reverse side" may be the entire region of the first sheet 201. In this case, the diffusive sub-sheet 201a may be omitted. However, in the case where the reverse surface of the first sheet 201 is composed of a sheet having a relatively high density, it is possible to suppress a situation where the powder S escapes to the reverse side through the first sheet 201, and thud efficiently arrange particles of the powder S within the first sheet 201. Further, as the first sheet 201, a sheet comprising a short fiber sub-sheet formed by processing other than air-through processing may be used. Further, as a non-woven fabric composing the entire region of the first sheet 201 or the given region from the obverse surface toward the reverse side of the first sheet 201, a non-woven fabric composed of long fibers may be used. However, the use of short fibers makes it possible to more reliably bury particles of the powder S inside the first sheet 201.

The second sheet 202 is not limited to a tissue paper. For example, it may be comprised of a non-woven fabric.

Although the above embodiments have been described based on an example where fibers of the first sheet 201 are entirely raised in the conveyance direction, only a partial zone of the first sheet 201 may be subjected to fiber-raising. For example, in the case where the powder S is supplied to only a width-directional intermediate zone of the first sheet 201, or supplied at given intervals in the width direction and/or the longitudinal direction of the first sheet 201, only such a powder supply zone to which the powder S is to be supplied may be subjected to fiber-raising. Alternatively, only part of the powder supply zone may be subjected to fiber-rising.

Although the above embodiments have been described based on an example in which fibers of the first sheet 201 are raised using the tiller 31, i.e., fibers of first sheet 201 are raised by rotating the cutter plates 33 each having the blades 34 formed in the outer peripheral face, and bringing the first sheet 201 into contact with the blades 34, the process and device for raising fibers of the first sheet 201 are not limited thereto.

For example, fibers of the first sheet 201 may be raised by rubbing the obverse surface of the first sheet with a friction material composed of a non-woven fabric.

Alternatively, in the fiber-raising device 30, one or more blades 34 are provided which protrude toward the obverse surface of the first sheet 201 and contact the obverse surface of the first sheet 201, in the same manner as that in the above embodiments, wherein the blades 34 may contact the first sheet 201 without moving the blades 34. Further, the blades 34 may be moved in a direction parallel to the conveyance direction of the first sheet 201, without rotationally moving the cutter plates 33. However, the above configuration using the tiller 31 makes it possible to raise fiber of the first sheet 201 with a simple configuration.

Further, even in the case using the tiller 31, a specific shape of each of the blade 34 is not limited to the aforementioned shape. For example, the upstream-side face and the downstream-side face of the blade 34 in the movement direction of the blades 34 may have the same shape. Further, the movement speed of the blades 34 is not limited to the aforementioned speed. Further, the number of blades 34 formed in each of the cutter plates 33 may be one. Further, the rotational speed and the rotational direction of the tiller 31 may be appropriately changed.

Although the above embodiments have been described based on an example in which the first sheet 201 is conveyed obliquely downwardly in a region beneath the distribution port 48c, the conveyance direction of the first sheet 201 is not limited thereto. For example, in the region beneath the distribution port 48c, the first sheet 201 may be conveyed horizontally or obliquely upwardly.

Although the above embodiments have been described based on an example in which the first sheet 201 and the second sheet 202 are pressure-joined by using the pressure-joining device 70, the process and device for pressure-joining the two sheets 201, 202 are not limited thereto. For example, in a situation where the guide roll (21, 121) is capable of sufficiently pressure-joining the two sheets 201, 202, the pressure-joining device 70 may be omitted.

Although the above embodiments have been described based on an example in which a hot-melt adhesive is used for bonding between the two sheets 201, 202, a specific configuration for bonding the two sheets 201, 202 together is not limited thereto. For example, the two sheets 201, 202 may be bonded together by means of heat-sealing or ultrasonic bonding.

Although the above embodiments have been described based on an example in which the metering unit 44 feeds the powder S downwardly at a given flow rate, this flow rate may be constant or may be temporally changed. For example, in the case where, it is necessary to place a larger amount of the powder S in a given zone of the first sheet in the conveyance direction Y1 of the first sheet 201, the flow rate may be increased at a timing corresponding to the given zone.

Further, a specific configuration of the metering unit 44 is not limited to the aforementioned configuration.

Although the above embodiments have been described based on an example in which the powder S is uniformly supplied in the width direction of the first sheet 201, a supply amount of the powder S to the first sheet S may be changed in the width direction of the first sheet 201.

For example, the powder guide section 47 may be divided, in the width direction of the first sheet 201, into a plurality of discrete passages, such that the powder S falls downwardly through respective ones of the discrete passages. Further, at least part of the powder S passing through some of the discrete passages may be appropriately removed from the some passages by removing means (mechanical means, blow means using airflow, or suction means) to change the supply amount of the powder S to the first sheet S in the width direction of the first sheet 201.

Although the above embodiments have been described based on an example in which the powder S is intermittently supplied to the first sheet 201, the powder S may be continuously supplied to the first sheet 201. However, in the case where the powder S is intermittently supplied to the first sheet 201 to provide specific zones devoid of the powder 5, on the first sheet 201, the first sheet 201 can be cut in each of the specific zones. In this case, it is possible to suppress leakage of the powder S through the resulting cut surface. In addition, it is possible to suppress damage to a cutter plate for use in the cutting, due to interference with particles of the powder S.

Further, a specific configuration for supplying the powder S to the first sheet 201 is not limited to the aforementioned configuration.

The above embodiments have been described based on an example in which a sheet having a width greater than that of the first sheet 201 is used as the second sheet 202, and the first sheet 201 is enfolded by such a second sheet 202. Alternatively, a sheet having the same width as that of the first sheet 201 may be used as the second sheet 202, and placed on the obverse surface of the first sheet 201. However, the configuration in which the first sheet 201 is enfolded by the second sheet 202 as mentioned above makes it possible to suppress leakage of the powder S from the width-directional opposite ends of the first sheet 201.

The above embodiments have been described based on an example in which, by the second adhesive application device 84, an adhesive is applied onto the width-directional opposite end portions of the second sheet 202, and, by the folding device 60, the second sheet 202 applied with the adhesive is folded, and bonded to the first sheet 201. Alternatively, an adhesive may be applied onto one of the width-directional opposite end portions of the second sheet 202 by the second adhesive application device 84, and the second sheet 202 applied with the adhesive may be folded by the folding device 60, such that the width-directional opposite end portions of the second sheet 202 are superimposed on each other on the first sheet 201 and bonded together, whereby the first sheet 201 can be enfolded by the second sheet 202.

The above embodiments have been described based on an example in which an adhesive is applied to the second sheet 202 to bond the first sheet 201 and the second sheet 202 together. Alternatively, a third adhesive application device may be disposed between the fiber-raising device 30 and the powder supply device 40, wherein after applying an adhesive to the obverse surface of the first sheet 201 whose fibers have been raised by the fiber-raising device, by means of spraying or the like, the powder S may be supplied to the obverse surface of the first sheet 201 applied with the adhesive. In this case, at least part of particles of the powder S are fixed to the first sheet 201 by the adhesive, so that it is possible to further suppress the displacement of particles of the powder S.

The above specific embodiments mainly include inventions having the following features.

The present invention provides an apparatus for manufacturing a powder-containing article containing a powder. The apparatus comprises: a sheet conveyance device which conveys, along a conveyance path, a sheet in which a given region from an obverse surface toward a reverse side thereof is composed of a non-woven fabric; a powder supply device which is provided on the conveyance path, and supplies the powder to at least a partial zone of the sheet, from an obverse side of the sheet; and a fiber-raising device which is provided on the conveyance path at a position upstream, in a conveyance direction of the sheet, of a powder supply position where the powder is supplied to the sheet, and raises fibers in at least part of the powder supply zone of the sheet, from the obverse side of the sheet.

According to this feature, fibers in at least part of the powder supply zone of the sheet in which a given region from the obverse surface toward the reverse side thereof is composed of a non-woven fabric are raised, so that inter-fiber spaces can be formed in the powder supply zone. Thus, when the powder is supplied to the powder supply zone from the obverse side, particles of the powder can be buried in the inter-fiber spaces, and fibers of the sheet can be interposed between respective ones of the powder particles. Therefore, it is possible to restrict free displacement of the powder particles by the fibers, and thus manufacture a powder-containing article in which the powder particles are stably arranged at adequate positions. Further, the fibers can be interposed between respective ones of the powder particles, so that it is possible to suppress a situation where the powder is biased to one area, i.e., to moderately disperse the powder particles.

Further, the powder particles can be buried in the inter-fiber spaces as mentioned above, so that it is possible to suppress a situation where, when the powder is supplied to the sheet, the powder particles bounces from the sheet, thereby efficiently supplying the powder to the sheet.

Preferably, the apparatus of the present invention comprises: a second sheet supply section which is provided on the conveyance path, and supplies a second sheet to the obverse surface of the sheet, at the powder supply position, or a position downstream, in the conveyance direction of the sheet, of the powder supply position; and a bonding device which is provided on the conveyance path, and bonds the sheet and the second sheet together at a second sheet supply position where the second sheet is supplied to the obverse surface of the sheet by the second sheet supply section, or a position downstream, in the conveyance direction of the sheet, of the second sheet supply position.

According to this feature, the second sheet is supplied to the obverse surface of the sheet supplied with the powder, and the two sheets are bonded together to confine the powder in the sheet by the second sheet, so that it is possible to suppress leakage of the powder from the obverse surface of the sheet.

Preferably, the above apparatus comprises a pressure joining device which is provided on the conveyance path at a position downstream, in the conveyance direction of the sheet, of the bonding device, and pressure-joins an assembly of the sheet and the second sheet in a thickness direction thereof.

According to this feature, the thickness of the sheet increased by the fiber-raising can be reduced again while restricting displacement of the powder particles by the raised fibers of the sheet, so that it is possible to manufacture a powder-containing article whose thickness is kept down. Further, by keeping down the thickness of the sheet, a space for allowing displacement of the powder particles is narrowed, so that it is possible to more reliably restrict the free displacement of the powder particles.

Preferably, in the above apparatus of the present invention, the bonding device bonds the sheet and the second sheet together while pressure joining them in their thickness direction.

According to this feature, while the second sheet is supplied to the obverse surface of the sheet, the two sheets can be bonded together and press joined by the bonding device, so that it is possible to structurally simplify the entire apparatus.

Preferably, in the apparatus of the present invention, the fiber-raising device comprises one or more blades each protruding toward the obverse surface of the sheet to contact the sheet, and wherein the sheet conveyance device conveys the sheet such that the sheet is moved relative to the one or more blades.

According to this feature, fibers of the sheet can be raised by a simple configuration in which the obverse surface of the sheet is scratched by the one or more blades provided in the fiber-raising device.

Preferably, in the above apparatus of the present invention, the fiber-raising device comprises a drive section which moves the one or more blades from an upstream side toward a downstream side of the conveyance direction of the sheet, at a movement speed less than a movement speed of the sheet.

According to this feature, the relative speed of the obverse surface of the sheet with respect to the one or more blades can be kept down while the conveyance speed of the sheet is maintained at a relatively high value, so that it is possible to more reliably suppress damage to the sheet when the one or more blades are engaged with the sheet.

Specifically, when the one or more blades are moved in a direction opposite to the conveyance direction of the sheet while the conveyance direction of the sheet is maintained at a relatively high value, the relative speed of the sheet with respect to the one or more blades is excessively increased, so that the one or more blades are likely to be excessively engaged with the sheet, leading to damage to the sheet.

Compared with this, according to the above feature, a movement direction of the one or more blades is set to be the same as the conveyancer direction of the sheet. Thus, the relative speed of the sheet with respect to the one or more blades can be kept down, so that it is possible to suppress excessive engagement of the sheet with the one or more blades.

As the configuration in which under the one or more blades are engaged with the sheet under the condition that the movement direction of the one or more blades is set to be the same as the conveyance direction of the sheet, it is conceivable that the movement speed of the one or more blades is set to be greater than the conveyance speed of the sheet, and the sheet is moved relative to the one or more blades, from the downstream side to the upstream side of the movement direction of the one or more blades, wherein the sheet is engaged with a portion of each of the one or more blades on the downstream side of the movement direction of the one or more blades, to this case, it is necessary to move the one or mode blades at a relatively high speed, and fibers of the sheet are less likely to be raised, because when each of the one or more blades comes into contact with the sheet, fibers of the sheet are pushed by the blade, toward the conveyance direction, of the sheet in a laying manner.

Compared with this, according to above feature, the movement direction of the one or more blades is set to be the same as the conveyance direction Y1 of the sheet, and the movement speed of the one or more blades is set to be less than the conveyance speed of the sheet. Thus, the sheet is moderately engaged with each of the one or more blades while the conveyance speed of the sheet is maintained at a relatively high value, so that fibers of the sheet can be successfully raised. According to the above feature, the sheet is moved relative to the one or more blades, from the downstream side to the upstream side of the movement direction of the one or more blades, wherein the sheet is engaged with an upstream-side portion of each of the one or more blades.

Preferably, in the above apparatus of the present invention, the drive section rotationally drives the one or more blades along a circumferential plane of a circular cylinder having a center line which is a line extending in a direction orthogonal to the conveyance direction of the sheet and parallel to the obverse surface of the sheet; and each of the one or more blades has a first face facing the upstream side of the conveyance direction of the sheet at a contact position with the sheet, and a second face facing the downstream side of the conveyance direction of the sheet at the contact position, wherein the first face has a shape extending in a radial direction of the circular cylinder, and the second face has a shape extending from an outer edge of the first face in the radial direction of the circular cylinder, toward a downstream side of the movement direction of the one or more blades and an inward side of the radial direction of the circular cylinder.

According to this feature, the radially-outer edge of each of the one or more blades which is a portion capable of scratching the sheet is formed in a shape sharp-edged toward an outward side of the radial direction, so that the outer edge of the blade can be engaged with the sheet to adequately raise fibers of the sheet. Further, the first face extends in the radial direction, so that, when the blade is separated from the sheet, fibers of the sheet are more likely to be released from the blade, so that it is possible to adequately convey the sheet while adequately raising fibers of the sheet.

Preferably, in the apparatus of the present invention, the powder supply device has a distribution port for distributing the powder over the sheet from the obverse side of the sheet, and wherein the apparatus for manufacturing a powder-containing article containing, a powder comprises a suction device which suctions the sheet from the reverse side, of the sheet, in at least part of a region from a position opposed to the distribution port to a position downstream of the opposed position in the conveyance direction of the sheet.

According to this feature, the powder particles can be reliably buried in the inter-fiber spaces and stably held inside the sheet. Specifically, if the sheet is suctioned from the reverse side thereof by the suction device before supplying the powder, raised fibers of the sheet are likely to lie down due to a suction force of the suction device, leading to breakage of the inter-fiber spaces. Compared with this, according to the above feature, at the same time or after the powder is supplied to the sheet, the sheet is suctioned from the reverse side thereof, so that it is possible to suppress breakage of the inter-fiber spaces and more reliably bury the powder particles in the inter-fiber spaces.

Preferably, in the above apparatus of the present invention, the sheet conveyance device conveys the sheet obliquely downwardly with respect to a vertical direction, at the opposed position.

According to this feature, the direction of the powder particles moving vertically downwardly by gravity becomes close to the movement direction of the sheet, so that it is possible to suppress a situation where the powder particles bounce from the sheet and drop out of the sheet, and thus efficiently supply the powder to the sheet.

The present invention further provides a method for manufacturing a powder-containing article containing a powder. The method comprises: a conveyance step of conveying, along a conveyance path, a sheet in which a given region from an obverse surface toward a reverse side thereof is composed of a non-woven fabric; a powder supply step of supplying the powder to at least a partial zone of the sheet being conveyed along the conveyance path, from an obverse side of the sheet; and a fiber-raising step of raising, from the obverse side of the sheet, fibers in at least part of the powder supply zone of the sheet being conveyed along the conveyance path, at a position of the conveyance path upstream, in a conveyance direction of the sheet, of a powder supply position where the powder is supplied to the sheet.

In this method, fibers in at least part of the powder supply zone of the sheet are raised, so that inter-fiber spaces can be formed in the powder supply zone. Thus, when the powder is supplied to the powder supply zone from the obverse side, particles of the powder can be buried in the inter-fiber spaces, and fibers of the sheet can be interposed between respective ones of the powder particles. Therefore, it is possible to restrict free displacement of the powder particles by the fibers, and thus manufacture a powder-containing article in which the powder particles are stably arranged at adequate positions. Further, the fibers can be interposed between respective ones of the powder particles, so that it is possible to suppress a situation where the powder is biased to one area, to moderately disperse the powder particles.

Further, the powder particles can be buried in the inter-fiber spaces as mentioned above, so that it is possible to suppress a situation where, when the powder is supplied to the sheet, the powder particles bounces from the sheet, and thus efficiently supply the powder to the sheet.

Preferably, the method of the present invention comprises: a second sheet supply step of supplying a second sheet to the obverse surface of the sheet being conveyed along the conveyance path, at the powder supply position, or a position downstream, in the conveyance direction of the sheet, of the powder supply position; and a bonding step of bonding the sheet and the second sheet supplied to the obverse surface of the sheet, together.

According to this feature, the second sheet is supplied to the obverse surface of the sheet supplied with the powder, and the two sheets are bonded together to confine the powder in the sheet by the second sheet, so that it is possible to suppress leakage of the powder from the obverse surface of the sheet.

Preferably, the above method of the present invention comprises a pressure-joining step of pressure-joining an assembly of the sheet being conveyed along the conveyance path and the second sheet bonded to the sheet, in a thickness direction thereof.

According to this feature, the thickness of the sheet increased by the fiber-raising can be reduced again while restricting displacement of the powder particles by the raised fibers of the sheet, so that it is possible to manufacture a powder-containing article whose thickness is kept down. Further, by keeping down the thickness of the sheet, a space for allowing displacement of the powder particles is narrowed, so that it is possible to more reliably restrict the free displacement of the powder particles.

Preferably, in the above method of the present invention, the bonding step includes bonding the sheet and the second sheet together while pressure joining them in their thickness direction.

According to this feature, while the second sheet is supplied to the obverse surface of the sheet, the two sheets can be bonded together and press-joined, so that it is possible to simplify a manufacturing process.

Preferably, the method of the present invention comprises a preparation step of, prior to the conveyance step, preparing a sheet whose portion to be subjected to fiber-raising in the fiber-raising step is comprised of a non-woven fabric composed of short fibers.

According to this feature, upon being subjected to fiber-raising, distal ends of raised fibers of the sheet are more exposed to the obverse side of the sheet, so that inter-fiber spaces can be opened on the obverse side of the sheet. Thus, through the resulting openings, particles of the powder can be arranged more deeply toward the reverse side in the sheet, so that it is possible to more reliably arrange the powder particles, respectively, in the inter-fiber spaces. Therefore, fibers of the sheet can be more reliably interposed between respective ones of the powder particles, so that it is possible to more reliably suppress the displacement of the powder particles by the fibers, and moderately disperse the powder particles. The term "short fiber" here means a fiber having a fiber length of less than 100 mm, preferably less than 80 mm, more preferably less than 70 mm, as measured by the average fiber length measurement method (C method) defined in JIS 1015.

LIST OF REFERENCE SIGNS

1: powder-containing article manufacturing apparatus
2: powder-containing article
10: first sheet conveyance device sheet cony a device)
20: second sheet conveyance device
21: guide roll (second sheet supply section, bonding; device)
30: fiber-raising device
40: powder supply device
60: bonding device
70: pressure-joining device
201: first sheet (sheet)
202: second sheet
S: powder

The invention claimed is:

1. An apparatus for manufacturing a powder-containing article containing a powder, comprising:
   a sheet conveyance device configured to convey, along a conveyance path, a sheet in which a given region from an obverse surface toward a reverse side thereof is composed of a non-woven fabric;
   a powder supply device provided on the conveyance path, the powder supply device being configured to supply the powder to at least a partial zone of the sheet, from an obverse side of the sheet; and
   a fiber-raising device provided on the conveyance path at a position upstream, in a conveyance direction of the sheet, of a powder supply position where the powder is supplied to the sheet, and the fiber-raising device being configured to raise fibers in at least part of the powder supply zone of the sheet, from the obverse side of the sheet,
   wherein the fiber-raising device comprises one or more blades each protruding toward the obverse surface of the sheet to contact the sheet, and wherein the sheet conveyance device is configured to convey the sheet such that the sheet is moved relative to the one or more blades.

2. The apparatus according to claim 1, wherein the sheet is a first sheet, the apparatus further comprising:
   a sheet supply section provided on the conveyance path, the sheet supply section being configured to supply a second sheet to the obverse surface of the first sheet, at the powder supply position, or a position downstream, in the conveyance direction of the sheet, of the powder supply position; and
   a bonding device provided on the conveyance path, the bonding device being configured to bond the first sheet and the second sheet together at a second sheet supply position where the second sheet is supplied to the obverse surface of the sheet by the sheet supply section, or a position downstream, in the conveyance direction of the sheet, of the second sheet supply position.

3. The apparatus according to claim 2, which comprises a pressure-joining device provided on the conveyance path at a position downstream, in the conveyance direction of the first sheet, of the bonding device, and pressure-joins an assembly of the first sheet and the second sheet in a thickness direction thereof.

4. The apparatus according to claim 2, wherein the bonding device bonds the first sheet and the second sheet together while pressure-joining them in their thickness direction.

5. The apparatus according to claim 1, wherein the fiber-raising device comprises a drive section configured to move the one or more blades from an upstream side toward a downstream side of the conveyance direction of the sheet, at a movement speed less than a movement speed of the sheet.

6. The apparatus according to claim 5, wherein:
the drive section is configured to rotationally drive the one or more blades along a circumferential plane of a circular cylinder having a center line which is a line extending in a direction orthogonal to the conveyance direction of the sheet and parallel to the obverse surface of the sheet; and
each of the one or more blades has a first face facing the upstream side of the conveyance direction of the sheet at a contact position with the sheet, and a second face facing the downstream side of the conveyance direction of the sheet at the contact position, wherein the first face has a shape extending in a radial direction of the circular cylinder, and the second face has a shape extending from an outer edge of the first face in the radial direction of the circular cylinder, toward a downstream side of the movement direction of the one or more blades and an inward side of the radial direction of the circular cylinder.

7. The apparatus according to claim 1, wherein the powder supply device has a distribution port for distributing the powder over the sheet from the obverse side of the sheet, and wherein the apparatus for manufacturing a powder-containing article containing a powder comprises a suction device configured to suction the sheet from the reverse side of the sheet, in at least part of a region from a position opposed to the distribution port to a position downstream of the opposed position in the conveyance direction of the sheet.

8. The apparatus according to claim 7, wherein the sheet conveyance device is configured to convey the sheet obliquely downwardly with respect to a vertical direction, at the opposed position.

9. A method for manufacturing a powder-containing article containing a powder, comprising:
conveying, along a conveyance path, a sheet in which a given region from an obverse surface toward a reverse side thereof is composed of a non-woven fabric;
supplying the powder to at least a partial zone of the sheet being conveyed along the conveyance path, from an obverse side of the sheet; and
raising, from the obverse side of the sheet, fibers in at least part of the powder supply zone of the sheet being conveyed along the conveyance path, at a position of the conveyance path upstream, in a conveyance direction of the sheet, of a powder supply position where the powder is supplied to the sheet;
wherein the raising of the fibers is performed by a fiber-raising device including one or more blades each protruding toward the obverse surface of the sheet to contact the sheet, and the conveying is performed so that the sheet is moved relative to the one or more blades.

10. The method according to claim 9, wherein the sheet is a first sheet, the method further comprising:
supplying a second sheet to the obverse surface of the first sheet being conveyed along the conveyance path, at the powder supply position, or a position downstream, in the conveyance direction of the first sheet, of the powder supply position; and
a bonding step of bonding the first sheet and the second sheet supplied to the obverse surface of the sheet, together.

11. The method according to claim 10, further comprising pressure joining an assembly of the first sheet being conveyed along the conveyance path and the second sheet bonded to the sheet, in a thickness direction thereof.

12. The method according to claim 10, wherein the bonding step includes bonding the first sheet and the second sheet together while pressure-joining them in their thickness direction.

13. The method according to claim 9, further comprising, prior to the conveyance step, preparing a sheet whose portion to be subjected to the raising of the fibers is comprised of a non-woven fabric composed of short fibers.

* * * * *